US006187786B1

(12) United States Patent
Venet et al.

(10) Patent No.: US 6,187,786 B1
(45) Date of Patent: Feb. 13, 2001

(54) FARNESYL TRANSFERASE INHIBITING 1,8-ANNELATED QUINOLINONE DERIVATIVES SUBSTITUTED WITH N- OR C-LINKED IMIDAZOLES

(75) Inventors: Marc Gaston Venet, Le Mesnil Esnard; Patrick René Angibaud, Fontaine-Bellenger; Yannick Aimé Eddy Ligny, Sotteville-lès-Rouen; Virginie Sophie Poncelet, Le Manoir sur Seine; Gerard Charles Sanz, Le Mesnil Esnard, all of (FR)

(73) Assignee: Janssen Pharmaceutica N.V., Beerse (BE)

( * ) Notice: Under 35 U.S.C. 154(b), the term of this patent shall be extended for 0 days.

(21) Appl. No.: 09/380,856

(22) PCT Filed: Mar. 3, 1998

(86) PCT No.: PCT/EP98/01296

§ 371 Date: Dec. 20, 1999

§ 102(e) Date: Dec. 20, 1999

(87) PCT Pub. No.: WO98/40383

PCT Pub. Date: Sep. 17, 1998

(30) Foreign Application Priority Data

Mar. 10, 1997 (EP) .................................... 97200708
Mar. 10, 1997 (EP) .................................... 97200709

(51) Int. Cl.⁷ .................. A61K 31/473; A61K 31/4738; C07D 471/06; C07D 498/06; A61P 35/00
(52) U.S. Cl. .................. 514/294; 514/230.2; 514/224.5; 514/291; 514/292; 514/293; 544/32; 544/101; 546/80; 546/82; 546/84; 546/89; 546/94
(58) Field of Search .................. 546/94, 89, 84, 546/82, 80; 544/32, 101; 514/291, 292, 293, 294, 230.2, 224.5

(56) References Cited

U.S. PATENT DOCUMENTS 4,014,883   3/1977   Fryer et al. ..................... 260/288

FOREIGN PATENT DOCUMENTS 0 371 559    6/1990   (EP) .
0 371 564    6/1990   (EP) .
1 394 373    5/1975   (GB) .
WO 93 25548  12/1993  (WO) .
WO 96 20200  7/1996   (WO) .

OTHER PUBLICATIONS

Khosravi–Far et al. Cell Growth & Differentiation. 3, 461–469, Jul. 1992.*
Njoroge et al. Bioorganic & Medicinal Chemistry. 5 (1), 101–113, 1997.*

* cited by examiner

Primary Examiner—Evelyn Mei Huang
(74) Attorney, Agent, or Firm—Myra McCormack

(57) ABSTRACT

This invention concerns compounds of formula

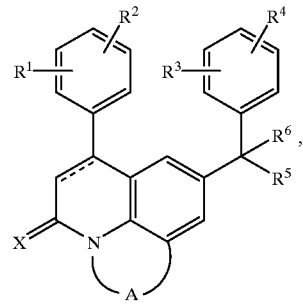

(I)

the pharmaceutically acceptable acid addition salts and the stereochemically isomeric forms thereof, wherein the dotted line represents an optional bond; X is oxygen or sulfur; —A— is a bivalent radical of formula; $R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino$C_{1-6}$alkyloxy, Ar, Ar—$C_{1-6}$alkyl, Ar-oxy, Ar—$C_{1-6}$alkyloxy; or when on adjacent positions $R^1$ and $R^2$ taken together may form a bivalent radical; $R^3$ and $R^4$ each independently are hydrogen, halo, cyano, $C_{1-6}$alkyl, $C_{1-6}$alkyloxy, Ar-oxy, $C_{1-6}$alkylthio, di($C_{1-6}$alkyl)amino, trihalomethyl, trihalomethoxy, or when on adjacent positions $R^3$ and $R^4$ taken together may form a bivalent radical; $R^5$ is an imidazolyl substituted with hydrogen or $C_{1-6}$alkyl; $R^6$ hydrogen, hydroxy, halo, cyano, optionally substituted $C_{1-6}$alkyl, $C_{1-6}$alkyloxycarbonyl or Ar; or a radical of formula —O—$R^7$, —S—$R^8$, —N—$R^8R^9$; and Ar is optionally substituted phenyl; having farnesyl transferase inhibiting activity; their preparation, compositions containing them and their use as a medicine.

11 Claims, No Drawings

FARNESYL TRANSFERASE INHIBITING 1,8-ANNELATED QUINOLINONE DERIVATIVES SUBSTITUTED WITH N- OR C-LINKED IMIDAZOLES

CROSS-REFERENCE TO RELATED APPLICATIONS

This application is the National Stage of PCT Application PCT/EP98/01296, filed Mar. 3, 1998 which claims priority from EP Patent Application No. 97.200.709.0, filed Mar. 10, 1997 and EP Patent Application No. 97.200.708.2, filed Mar. 10, 1997.

The present invention is concerned with novel 1,8-annelated 2-quinolinone derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the, precursor of the $p21^{ras}$ oncoprotein must undergo an enzymatically catalyzed farnesylation of the cysteine residue located in a carboxyl-terminal tetrapeptide. Therefore, inhibitors of the enzyme that catalyzes this modification, farnesyl protein transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated oncogenic forms of ras are frequently found in many human cancers, most notably in more than 50% of colon and pancreatic carcinomas (Kohl et al., *Science*, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

Unexpectedly, it has been found that the present novel compounds, all having a phenyl substituent on the 4-position of the 1,8-annelated 2-quinolinone-moiety bearing a nitrogen- or carbon-linked imidazole, show farnesyl protein transferase inhibiting activity.

The present invention concerns compounds of formula

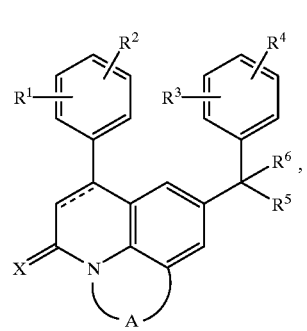

(I)

the pharmaceutically acceptable acid addition salts and the stereochemically isomeric forms thereof, wherein the dotted line represents an optional bond;

X is oxygen or sulfur;

—A— is a bivalent radical of formula

| —CH=CH— | (a-1), | —CH$_2$—S— | (a-6), |
|---|---|---|---|
| —CH$_2$—CH$_2$— | (a-2), | —CH$_2$—CH$_2$—S— | (a-7), |
| —CH$_2$—CH$_2$—CH$_2$— | (a-3), | —CH=N— | (a-8), |
| —CH$_2$—O— | (a-4), | —N=N— | (a-9), or |
| —CH$_2$—CH$_2$—O— | (a-5), | —CO—NH— | (a-10); | wherein optionally one hydrogen atom may be replaced by $C_{1-4}$alkyl or $Ar^1$;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino $C_{1-6}$alkyloxy, $Ar^2$, $Ar^2$—$C_{1-6}$alkyl, $Ar^2$-oxy, $Ar^2$—$C_{1-6}$alkyloxy;

or when on adjacent positions $R^1$ and $R^2$ taken together may form a bivalent radical of formula

| —O—CH$_2$—O— | (b-1), |
|---|---|
| —O—CH$_2$—CH$_2$—O— | (b-2), |
| —O—CH=CH— | (b-3), |
| —O—CH$_2$—CH$_2$— | (b-4), |
| —O—CH$_2$—CH$_2$—CH$_2$— | (b-5), or |
| —CH=CH—CH=CH— | (b-6); |

$R^3$ and $R^4$ each independently are hydrogen, halo, cyano, $C_{1-6}$alkyl, $C_{1-6}$alkyloxy, $Ar^3$-oxy, $C_{1-6}$alkylthio, di($C_{1-6}$alkyl)amino, trihalomethyl, trihalomethoxy, or when on adjacent positions $R^3$ and $R^4$ taken together may form a bivalent radical of formula

| —O—CH$_2$—O— | (c-1), |
|---|---|
| —O—CH$_2$—CH$_2$—O— | (c-2), or |
| —CH=CH—CH=CH— | (c-3); |

$R^5$ is a radical of formula

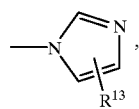

(d-1)

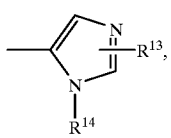

(d-2)

wherein $R^{13}$ is hydrogen, halo, $Ar^4$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, $C_{1-6}$alkyloxycarbonyl, $C_{1-6}$alkylS(O)$C_{1-6}$alkyl or $C_{1-6}$alkylS(O)$_2C_{1-6}$alkyl;

$R^{14}$ is hydrogen, $C_{1-6}$alkyl or di($C_{1-4}$alkyl)aminosulfonyl;

$R^6$ is hydrogen, hydroxy, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl$C_{1-6}$alkyl, $C_{1-6}$alkyloxycarbonyl$C_{1-6}$alkyl, $C_{1-6}$alkylcarbonyl-$C_{1-6}$alkyl, $C_{1-6}$alkyloxycarbonyl, mono- or di($C_{1-6}$alkyl)amino$C_{1-6}$alkyl, $Ar^5$, $Ar^5$—$C_{1-6}$alkyloxy$C_{1-6}$alkyl; or a radical of formula

| —O—$R^7$ | (e-1), |
| —S—$R^7$ | (e-2), |
| —N—$R^8R^9$ | (e-3), | wherein $R^7$ is hydrogen, $C_{1-6}$alkyl, $C_{1-6}$alkylcarbonyl, $Ar^6$, $Ar^6$—$C_{1-6}$alkyl, $C_{1-6}$alkyloxycarbonyl$C_{1-6}$alkyl, or a radical of formula —Alk—$OR^{10}$ or —Alk—$NR^{11}R^{12}$;

$R^8$ is hydrogen, $C_{1-6}$alkyl, $Ar^7$ or $Ar^7$—$C_{1-6}$alkyl;

$R^9$ is hydrogen, $C_{1-6}$alkyl, $C_{1-6}$alkylcarbonyl, $C_{1-6}$alkyloxycarbonyl, $C_{1-6}$alkylaminocarbonyl, $Ar^8$, $Ar^8$—$C_{1-6}$alkyl, $C_{1-6}$alkylcarbonyl-$C_{1-6}$alkyl, $Ar^8$—carbonyl, $Ar^8$—$C_{1-6}$alkylcarbonyl, aminocarbonylcarbonyl, $C_{1-6}$alkyloxy$C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—$OR^{10}$ or —Alk—$NR^{11}R^{12}$;

wherein Alk is $C_{1-6}$alkanediyl;

$R^{10}$ is hydrogen, $C_{1-6}$alkyl, $C_{1-6}$alkylcarbonyl, hydroxy$C_{1-6}$alkyl, $Ar^9$ or $Ar^9$—$C_{1-6}$alkyl;

$R^{11}$ is hydrogen, $C_{1-6}$alkyl, $C_{1-6}$alkylcarbonyl, $Ar^{10}$ or $Ar^{10}$—$C_{1-6}$alkyl;

$R^{12}$ is hydrogen, $C_{1-6}$alkyl, $Ar^{11}$ or $Ar^{11}$—$C_{1-6}$alkyl; and $Ar^1$ to $Ar^{11}$ are each independently selected from phenyl; or phenyl substituted with halo, $C_{1-6}$alkyl, $C_{1-6}$alkyloxy or trifluoromethyl.

$R^{13}$ may also be bound to one of the nitrogen atoms in the imidazole ring of formula (d-1). In that case the meaning of $R^{13}$ when bound to the nitrogen is limited to hydrogen, $Ar^4$, $C_{1-6}$alkyl, hydroxy$C_{1-6}$alkyl, $C_{1-6}$alkyloxy$C_{1-6}$alkyl, $C_{1-6}$alkyloxycarbonyl, $C_{1-6}$alkylS(O)—$C_{1-6}$alkyl or $C_{1-6}$alkylS(O)$_2C_{1-6}$alkyl.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, e.g. methyl, ethyl, propyl, butyl, 1-methylethyl, 2-methylpropyl and the like; $C_{1-6}$alkyl includes $C_{1-4}$alkyl and the higher homologues thereof having 5 to 6 carbon atoms such as, for example, pentyl, 2-methylbutyl, hexyl, 2-methylpentyl and the like; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; $C_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like. The term "S(O)" refers to a sulfoxide and "S(O)$_2$" to a sulfon.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Wherever —A— is a bivalent radical of formula (a-4), (a-5), (a-6), (a-7) or (a-8) the CH$_2$ or CH moiety in said bivalent radical is preferably connected to the nitrogen atom of the 2-quinolinone-moiety of the compounds of formula (I) or the intermediates of formula (II), (IV), (VI) and (VII).

Whenever used hereinafter, the term "compounds of formula (I)" is meant to include also the pharmaceutically acceptable acid addition salts and all stereoisomeric forms.

A group of interesting compounds consists of those compounds of formula (I) wherein one or more of the following restrictions apply:

a) the dotted line represents an optional bond;
b) X is O or S;
c) $R^1$ and $R^2$ are each independently selected from hydrogen, halo, $C_{1-6}$alkyl, $C_{1-6}$alkyloxy, trihalomethyl or trihalomethoxy; in particular hydrogen, halo or $C_{1-4}$alkyl;
d) $R^3$ and $R^4$ are each independently selected from hydrogen, halo, $C_{1-6}$alkyl, $C_{1-6}$alkyloxy, trihalomethyl or trihalomethoxy; in particular hydrogen, halo, $C_{1-4}$alkyl or $C_{1-4}$alkyloxy;
e) $R^5$ is a radical of formula (d-1) wherein $R^{13}$ is hydrogen or $C_{1-6}$alkyl; or $R^5$ is a radical of formula (d-2) wherein $R^{13}$ is hydrogen or $C_{1-6}$alkyl and $R^{14}$ is hydrogen or $C_{1-6}$alkyl;
f) $R^6$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, or a radical of formula —$NR^8R^9$ wherein $R^8$ is hydrogen or $C_{1-6}$alkyl and $R^9$ is hydrogen, $C_{1-6}$alkyl, $C_{1-6}$alkyloxy, $C_{1-6}$alkyloxy-$C_{1-6}$alkylcarbonyl; in particular $R^6$ is hydrogen, hydroxy, halo or a amino;
g) —A— is (a-1), (a-2), (a-3), (a-4), (a-5), (a-8), (a-9) or (a-10).

A particular group of compounds consists of those compounds of formula (I) wherein the dotted line represents a bond; X is O or S; $R^2$ is hydrogen and $R^1$ is halo, preferably chloro, especially 3-chloro; $R^4$ is hydrogen and $R^3$ is halo, preferably chloro, especially 4-chloro; $R^5$ is a radical of formula (d-1) wherein $R^{13}$ is hydrogen or $C_{1-4}$alkyl; and $R^6$ is hydrogen.

Another particular group of compounds consists of those compounds of formula (I) wherein the dotted line represent a bond; X is O or S; $R^2$ is hydrogen and $R^1$ is halo, preferably chloro, especially 3-chloro; and $R^4$ is hydrogen and $R^3$ is halo, preferably chloro, especially 4-chloro; $R^5$ is a radical of formula (d-2) wherein $R^{13}$ is hydrogen or $C_{1-4}$alkyl and $R^{14}$ is hydrogen or $C_{1-4}$alkyl; $R^6$ is hydrogen, hydroxy, halo or amino.

Preferred compounds are those compounds of formula (I) wherein the dotted line represents a bond; X is oxygen; $R^1$ is 3-chloro; $R^2$ is hydrogen; $R^3$ is 4-chloro; $R^4$ is hydrogen; $R^5$ is a radical of formula (d-1) wherein $R^{13}$ is hydrogen or $C_{1-4}$alkyl; $R^6$ is hydrogen, and —A— is (a-1), (a-2) or (a-3).

Other preferred compounds are those compounds of formula (I) wherein the dotted line represent a bond; X is oxygen; $R^1$ is 3-chloro; $R^2$ is hydrogen; $R^3$ is 4-chloro; $R^4$ is hydrogen; $R^5$ is a radical of formula (d-2) wherein $R^{13}$ is hydrogen and $R^{14}$ is $C_{1-4}$alkyl; $R^6$ is amino; and —A— is (a-1), (a-2) or (a-3).

The most preferred compounds of formula (I) are 7-(3-chlorophenyl)-9-[(4-chlorophenyl)-1H-imidazol-1-ylmethyl]-2,3-dihydro-1H,5H-benzo[ij]quinolizin-5-one,
7-(3-chlorophenyl)-9-[(4-chlorophenyl)-1H-imidazol-1-ylmethyl]-1,2-dihydro-4H-pyrrolo[3,2,1-ij]quinoline-4-one,
8-[amino(4-chlorophenyl)(1-methyl-1H-imidazol-5-yl), methyl]-6-(3-chlorophenyl)-1,2-dihydro-4H-pyrrolo[3,2,1-ij]quinolin-4-one, and
8-[amino(4-chlorophenyl)(1-methyl-1H-imidazol-5-yl) methyl]-6-(3-chlorophenyl)-2,3-dihydro-1H,5H-benzo[ij]quinolizin-5-one; the stereoisomeric forms and the pharmaceutically acceptable acid addition salts thereof.

The compounds of formula (I), wherein $R^6$ is hydroxy and $R^5$ is a radical of formula (d-2) wherein $R^{14}$ is $C_{1-6}$alkyl, said compounds being referred to as compounds of formula (I-a-1) may be prepared by reacting an intermediate ketone of formula (II) with a intermediate of formula (III-1). Said reaction requires the presence of a suitable strong base, such as, for example, butyl lithium in an appropriate solvent, such as, for example, tetrahydrofuran, and the presence of an appropriate silanederivative, such as, for example, triethylchlorosilane. During the work-up procedure an intermediate silane derivative is hydrolyzed. Other procedures with protective groups analogous to silanederivatives can also be applied.

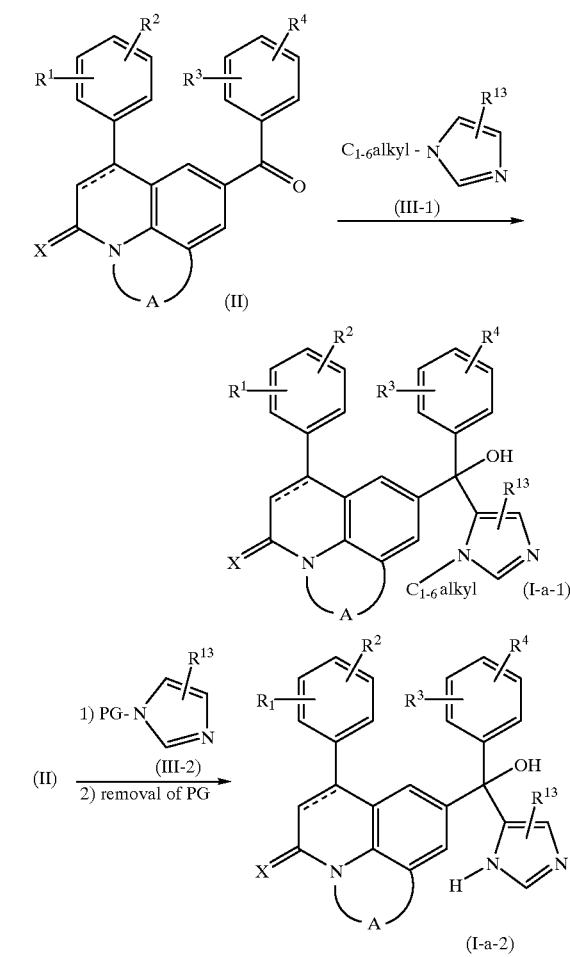

Also, the compounds of formula (I), wherein $R^6$ is hydroxy and $R^5$ is a radical of formula (d-2) wherein $R^{14}$ is hydrogen, said compounds being referred to as compounds of formula (I-a-2) may be prepared by reacting an intermediate ketone of formula (II) with a intermediate of formula (III-2), wherein PG is a protective group such as, for example, a sulfonyl group, e.g. a dimethylamino sulfonyl group, which can be removed after the addition reaction. Said reaction is conducted analogously as for the preparation of compounds of formula (I-a-1), followed by removal of the protecting group PG, yielding compounds of formula (I-a-2).

Compounds of formula (I-g), defined as compounds of formula (1) wherein $R^5$ represents a radical of formula (d-1), can be prepared by N-alkylating an intermediate of formula (XVIII) with an intermediate of formula (XVII), wherein W is an appropriate leaving group such as, for example, chloro, bromo, methanesulfonyloxy or benzenesulfonyloxy. The reaction can be performed in a reaction-inert solvent such as, for example, acetonitrile, and optionally in the presence of a suitable base such as, for example, sodium carbonate, potassium carbonate or triethylamine. Stirring may enhance the rate of the reaction. The reaction may conveniently be carried out at a temperature ranging between room temperature and the reflux temperature of the reaction mixture.

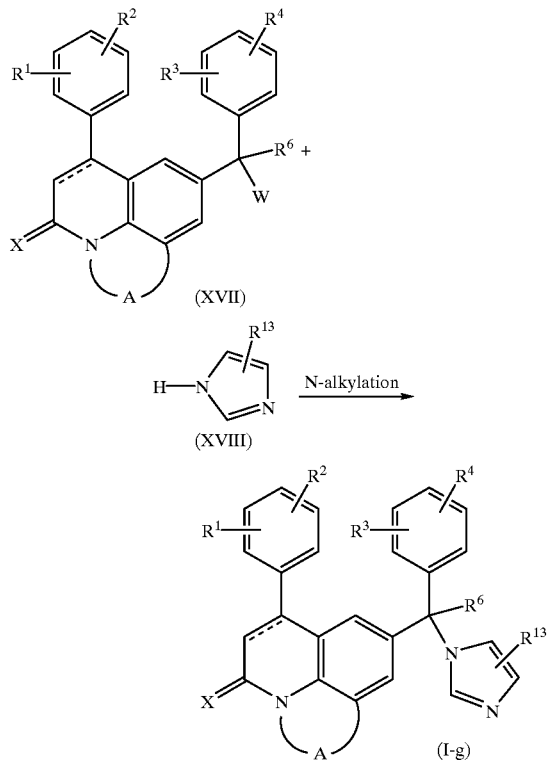

Also, compounds of formula (I-g) can be prepared by N-alkylating an intermediate of formula (XIX), wherein Y is carbon or sulfur, such as, for example, a 1,1'-carbonyldiimidazole, with an intermediate of formula (XVI).

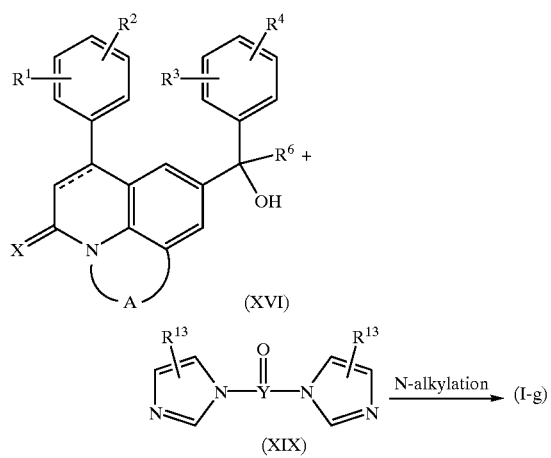

Said reaction may conveniently be conducted in a reaction-inert solvent, such as, e.g. tetrahydrofuran, optionally in the presence of a base, such as sodium hydride, and at a temperature ranging between room temperature and the reflux temperature of the reaction mixture.

Compounds of formula (I-g) may also be prepared by reacting an intermediate of formula (XVII) with ammonia and subsequent treatment with isothiocyanate as described in EP-0,293,978 page 12, line 33 to page 13, line 20.

The compounds of formula (I-a) can be converted to compounds of formula (I-b), defined as a compound of formula (I) wherein $R^6$ is hydrogen, by submitting the compounds of formula (I-a) to appropriate reducing conditions, such as, e.g. stirring in acetic acid in the presence of formamide.

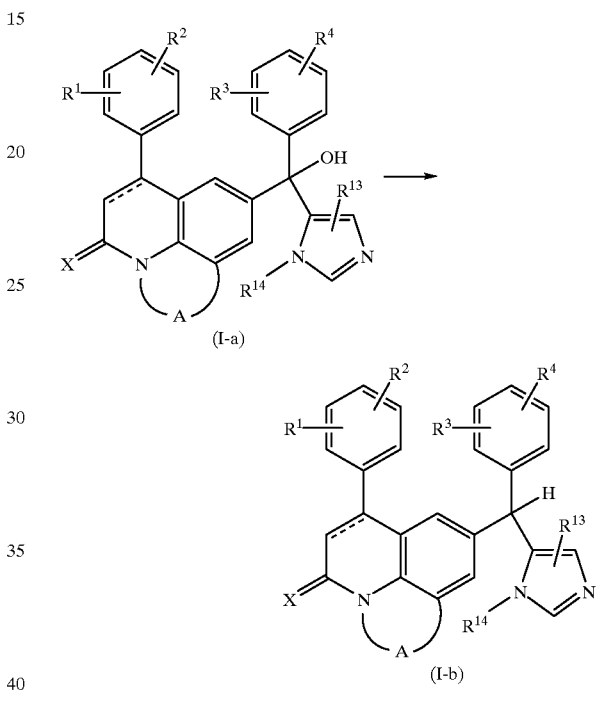

Further, compounds of formula (I-a) can be converted to compounds of formula (I-c) wherein $R^6$ is halo, by reacting the compounds of formula (I-a) with a suitable halogenating agent, such as, e.g. thionyl chloride or phosphorus tribromide. Successively, the compounds of formula (I-c) can be treated with a reagent of formula H—$NR^8R^9$ in a reaction-inert solvent, thereby yielding compounds of formula (I-d).

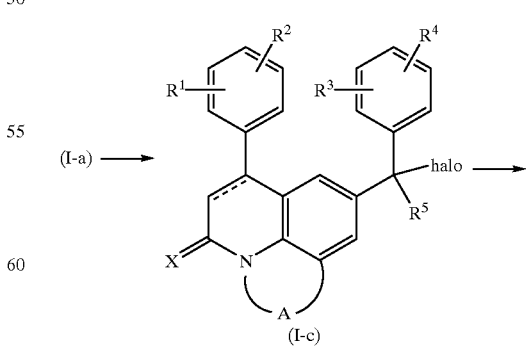

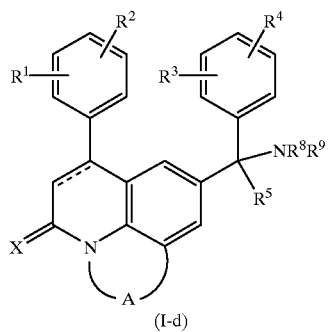

(I-d)

A compound of formula (I-f), defined as a compound of formula (I) wherein X is sulfur, may be prepared by reacting the corresponding compound of formula (I-e), defined as a compound of formula (I) wherein X is oxygen, with a reagent like phosphorus pentasulide or Lawesson's reagent in a suitable solvent such as, for example, pyridine.

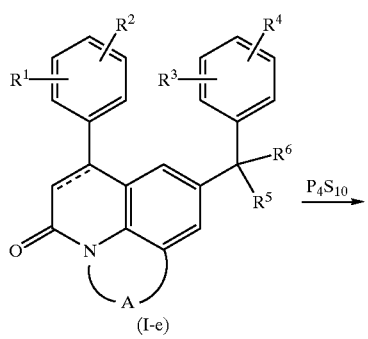

(I-e)

$P_4S_{10}$ (I-f)

An intermediate of formula (II-b), defined as an intermediate of formula (II) wherein the dotted line represents a bond, can be prepared by oxidizing an intermediate of formula (II-a), defined as intermediates of formula (II) wherein the dotted line does not represent a bond, following art-known oxidation methods such as, for example, treatment with bromine in an appropriate solvent such as, e.g. bromobenzene, or treatment with iodine in the presence of acetic acid and potassium acetate.

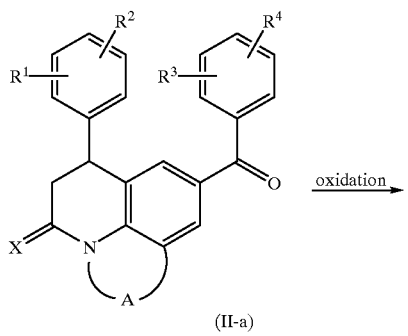

(II-a) oxidation (II-b)

Said oxidation reaction can give rise to side-products wherein the bivalent radical —A— is oxidized. For instance, oxidation of intermediates of formula (II-a) wherein —A— is (a-2) may give intermediates of formula (II-b) wherein —A— is (a-1).

Intermediates of formula (XVI) wherein $R^6$ is hydrogen, said compounds being represented by formula (XVI-a), can be prepared by reacting intermediates of formula (II) with an appropriate reducing agent such as, e.g. sodium borohydride, in a suitable solvent such as, e.g. methanol. Optionally, intermediates of formula (XVI) may be converted to intermediates of formula (XVII) wherein $R^6$ is hydrogen, said compounds being represented by formula (XVII-a), by treating (XVI-a) with a suitable reagent such as, e.g. methanesulfonyloxy chloride, or a halogenating reagent such as, e.g. $POCl_3$ or $SOCl_2$.

(II) reduction

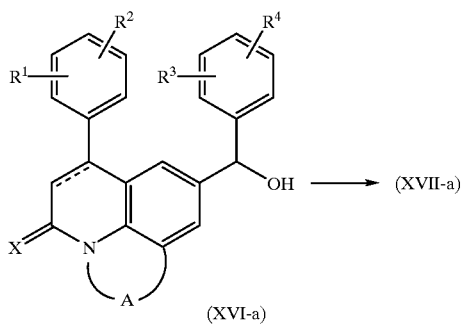

Intermediates of formula (II-a) can be prepared by reacting intermediates of formula (IV) with intermediates of formula (V) in the presence of polyphosphoric acid (PPA), at a temperature ranging between room temperature and the reflux temperature of the reaction mixture. Optionally said reaction may be performed in a reaction-inert solvent.

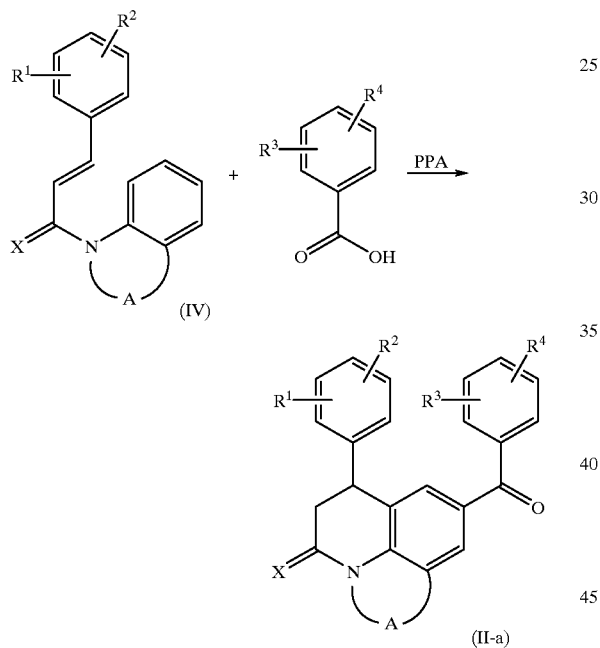

Alternatively, an intermediate of formula (II-a) can be made in a two-step synthesis by cyclizing an intermediate of formula (IV) in the presence of polyphosphoric acid (PPA) and subsequent treating the thus obtained intermediate (VI) with an intermediate of formula (VII) in the presence of PPA. Said two-step synthesis may be conducted in a "one-pot" synthesis or, if desired, intermediates of formula (VI) may be isolated and purified before reaction with intermediates of formula (V).

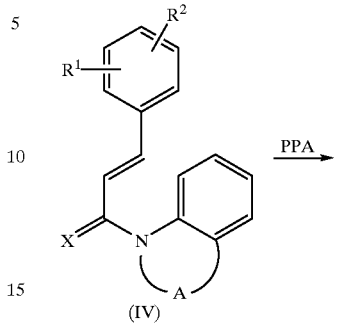

Intermediates of formula (IV) can be prepared by treating intermediates of formula (VIII), wherein X is oxygen or sulfur and Z is hydroxy or halo, with an intermediate of formula (VII) in a reaction-inert solvent such as, e.g. dichloromethane, and in the presence of a base such as, e.g. triethylamine, to pick up the acid liberated during the reaction.

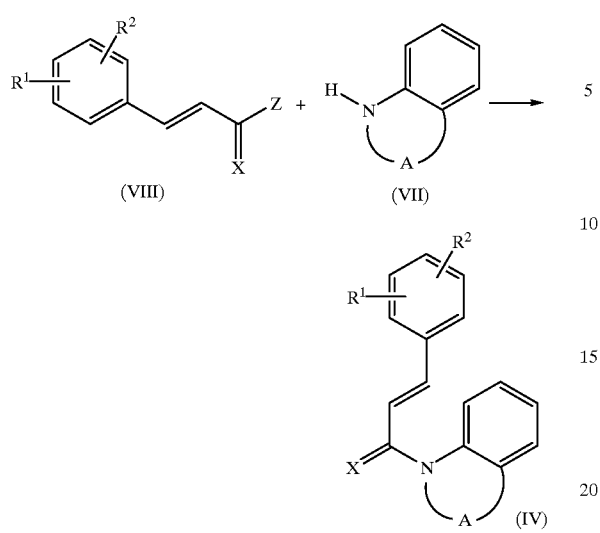

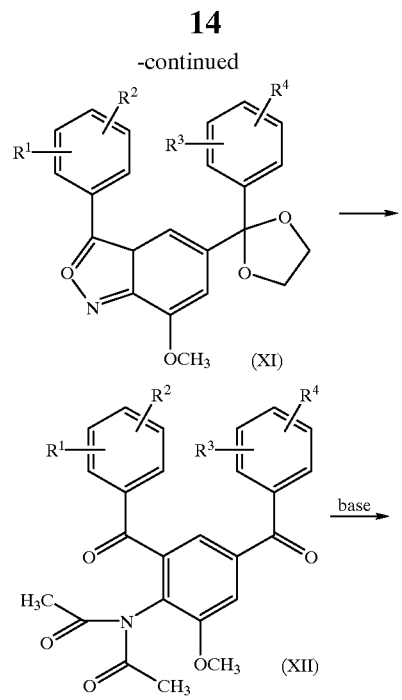

Intermediates of formula (II-b-1), being intermediates of formula (II-b) wherein X is oxygen and —A'— is a bivalent radical of formula (a-4) or (a-5), can be prepared starting from an intermediate of formula (IX). Said intermediates (IX) are conveniently prepared by protecting the corresponding art-known ketones. Intermediates of formula (IX) are stirred with intermediates of formula (X) in the presence of a base such as sodium hydroxide, in an appropriate solvent, such as an alcohol, e.g. methanol. The thus obtained intermediates of formula (XI) are converted to intermediates of formula (XII) in the presence of a suitable reagent such as, an acid, e.g. $TiCl_3$, in the presence of water; or by hydrogenation under acidic conditions in the presence of a suitable catalyst e.g. platinum on carbon; and by subsequent treatment with acetic anhydride. Intermediates of formula (XII) undergo ring closure in the presence of a base such as, for example, potassium tert-butoxide, and subsequently hydrolysis, yielding intermediates of formula (XIII). After conversion of the methoxy group of intermediates of formula (XVIII) into hydroxy, by treatment with a suitable agent such as, e.g. borontribromide, the intermediates of formula (XIV) are treated with an intermediate of formula (XV), wherein A' is a bivalent radical of formula (a-4) or (a-5), thereby yielding intermediates of formula (II-b-1).

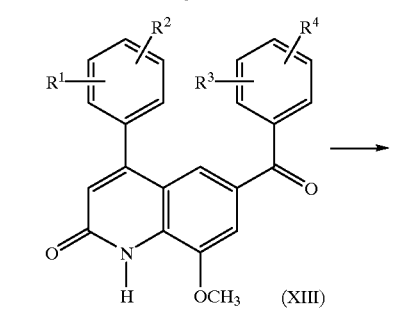

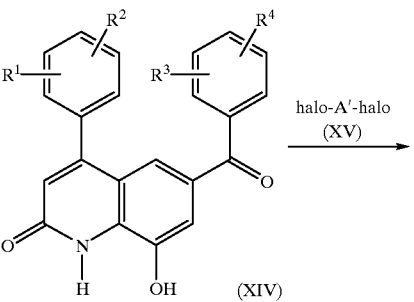

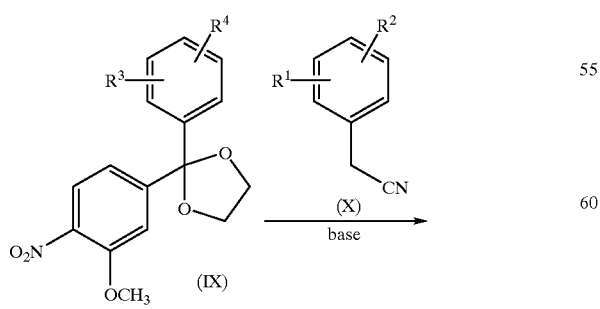

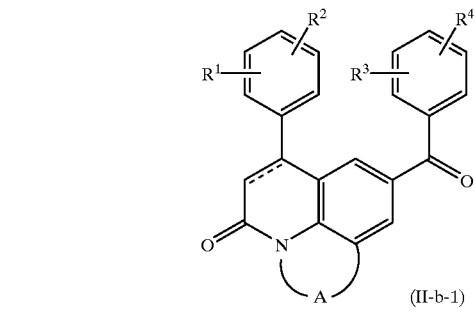

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable acid addition salts and stereoisomeric forms thereof have valuable pharmacological properties in that they inhibit farnesyl protein transferase (FPTase), as can be evidenced by the results obtained in the pharmacological examples C-1 and C-2.

Furthermore, it is believed that the compounds of formula (I) wherein $R^5$ is a radical of formula (d-2) can also inhibit geranylgeranyltransferase (GGTase).

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of of tumors in vivo by a direct effect on tumor cell growth but also indirectly, i.e. by facilitating tumor-induced angiogenesis (Rak. J. et al, *Cancer Research,* 55, 4575–4580, 1995). Hence, pharmacologically targetting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma, kidney carninoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes, i.e. the ras gene itself is not activated by mutation to an oncogenic form, with said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes may be inhibited by the compounds of this invention.

Hence, the present invention discloses the compounds of formula (I) for use as a medicine as well as the use of these compounds of formula (I) for the manufacture of a medicament for treating one or more of the above mentioned conditions.

In view of their useful pharmacological properties, the subject compounds may be formulated into various pharmaceutical forms for administration purposes.

To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.01 mg/kg to 100 mg/kg body weight, and in particular from 0.05 mg/kg to 10 mg/kg body weight. It may be appropriate to administer the required dose as two, three, four or more sub-doses at appropriate intervals throughout the day. Said sub-doses may be formulated as unit dosage forms, for example, containing 0.5 to 500 mg, and in particular 1 mg to 200 mg of active ingredient per unit dosage form.

The following examples are provided for purposes of illustration.

Experimental Part

Hereinafter "ACN" means acetonitrile, "THF" means tetrahydrofuran, "DIPE" means diisopropylether, "DCM" means dichloromethane and "DMF" means N,N-dimethylformamide.

Of some compounds of formula (I) the absolute stereochemical configuration was not experimentally determined. In those cases the stereochemically isomeric form which was first isolated is designated as "A" and the second as "B", without further reference to the actual stereochemical configuration.

A. Preparation of the Intermediates

EXAMPLE A.1

Triethylamine (9.2 ml) was added at room temperature to a solution of indoline (20 g) in DCM (200 ml) and the mixture was cooled till 5° C. A solution of m-chlorocinnamoyl chloride (40 g) in DCM (100 ml) was added dropwise and the mixture was stirred at room temperature for 48 hours. Water was added, the organic layer was decanted, washed with water, dried, filtered off and evaporated. The residue was purified by column chromatography over silica gel (eluent: cyclohexane/ethyl acetate 90/10), yielding 41 g (73%) of 1-[3-(3-chlorophenyl)-1-oxo-2-propenyl]-2,3-dihydro-1H-indole (interm. 37).

In a similar way, 1-[3-(3-chlorophenyl)-1-oxo-2-propenyl]-1,2,3,4-tetrahydroquinoline (interm. 38) was synthesized.

EXAMPLE A.2

Intermediate 37 (40 g) and polyphosphoric acid (350 g) were stirred and heated at 140° C. for 16 hours. 4-Chlorobenzoic acid (44 g) was added and the solution was stirred and heated at 140° C. for 2 hours and 30 minutes. The mixture was cooled till 80° C., ice was added carefully and the mixture was brought till room temperature. The precipitate was filtered off, washed with water and basified with an aqueous ammonia solution. The precipitate was taken up in DCM and filtered off. The organic layer was dried, filtered and evaporated. The residue was purified by column chromatography over silica gel (eluent: $CH_2Cl_2/CH_3OH$ 99.5/0.5 to 99/1), yielding 12 g (20%) of (±)-8-(4-chlorobenzoyl)-6-(3-chlorophenyl)-1,2,5,6-tetrahydro-4H-pyrrolo[3,2,1-ij]quinolin-4-one (interm. 11).

In a similar way, (±)-9-(4-chlorobenzoyl)-7-(3-chlorophenyl-2,3,6,7-tetrahydro-1H,5H-benzo[ij]quinolizin-5-one (interm. 8) was synthesized.

EXAMPLE A.3

A mixture of bromine (4.2 ml) in bromobenzene (80 ml) was added dropwise at room temperature to a solution of intermediate 11 (34.2 g) in bromobenzene (300 ml). The mixture was stirred and refluxed overnight. The mixture was cooled to room temperature and basified with an aqueous ammonia solution. The solvent was evaporated. The residue was partitioned between DCM and water. The organic layer was separated, dried, filtered and the solvent was evaporated. The residue was purified by column chromatography over silica gel (eluent: DCM). Two fractions were collected, yielding 16 g of 8-(4-chlorobenzoyl)-6-(3-chlorophenyl)-1,2-dihydro-4H-pyrrolo[3,2,1-ij]quinolin-4one (intermediate 24) and 2.1 g (6.2%) of 8-(4-chlorobenzoyl)-6-(3-chlorophenyl)-4H-pyrrolo[3,2,1-ij]quinolin-4-one (interm. 25).

EXAMPLE A.4

A mixture of intermediate (9) (20.9 g), iodine (32.8 g) and potassium acetate (19 g) in acetic acid (150 ml) was stirred at 130° C. for 3 days. The mixture was poured out warm on ice and $NaHSO_3$ and extracted with DCM. The organic layer was separated, dried, filtered and the solvent was evaporated till dryness. The residue was purified by column chromatography over silica gel (eluent: $CH_2Cl_2/CH_3OH$ 99/1 to 97/3. The pure fractions were collected and the solvent was evaporated. The residue was taken up in diethyl ether, filtered off and dried, yielding 16.9 g (81%) of 8-(4-chlorobenzoyl)-1,2-dihydro-6-phenyl-4H-pyrrolo[3,2,1 -ij] quinolin-4-one (interm. 21).

EXAMPLE A.5 a) A mixture of (4-chlorophenyl)(3-methoxy-4-nitrophenyl)methanone (40.7 g), 1,2-ethanediol (31.2 ml) and 4-methylbenzene sulfonic acid (5.31 g) in methylbenzene (320 ml) was stirred and refluxed using a Dean-Stark apparatus. The mixture was washed with $K_2CO_3$ (10%) and extracted with DCM. The organic layer was separated, dried, filtered and the solvent was evaporated. The residue was crystallized from DIPE. The precipitate was filtered off and dried, yielding 22.48 g (50.4%) of 2-(4-chlorophenyl)-2-(3-methoxy-4-nitrophenyl)-1,3-dioxolane (interm. 39).

b) Intermediate (39) (22.48 g) and 3-chlorobenzenacetonitrile (15 ml) were added to a solution of sodium hydroxide (11.25 g) in methanol (91 ml). The mixture was stirred and refluxed for 24 hours. Ice water was added. The precipitate was filtered off, washed with water and with ethanol and dried. The residue was purified by column chromatography over silica gel (eluent: $CH_2Cl_2$/cyclohexane 60/40). The pure fractions were collected and the solvent was evaporated, yielding 8.5 g (27.3%) of 3-(3-chlorophenyl)-5-[2-(4-chlorophenyl)-1,3-dioxolan-2-yl]-7-methoxy-2,1-benzisoxazole (interm. 40).

c) A mixture of intermediate (40) (14 g) in HCl conc. (3.5 ml) and THF (140 ml) was hydrogenated under a $2.4 \times 10^5$ Pa (2.4 bar) pressure for 6 hours with platinum on carbon (5%; 1.4 g) as a catalyst in the presence of a 10% solution of thiophene in methanol (0.35 ml). After uptake of adequate $H_2$, the catalyst was filtered through celite and the filtrate was evpaorated till dryness. The residue was taken up in 2-propanone and DIPE. The precipitate was filtered off and dried, yielding 11.8 g (84.3%) of [2-amino-5-(4-chlorobenzoyl)-3-methoxyphenyl](3-chlorophenyl)methanone (interm. 41).

d) A mixture of intermediate (41) (11.7 g) and acetic anhydride (28 ml) in toluene (150 ml) was stirred and refluxed for 24 hours. The solvent was evaporated till dryness. The product was used without further purification, yielding 14.5 g of N-acetyl-N-[2-(3-chlorobenzoyl)-4-(4-chlorobenzoyl)-6-methoxyphenyl]acetamide (interm. 42)

e) Potassium-tert-butoxide (13.5 g) was added portionwise to a mixture of intermediate (42) (14.5 g) in dimethyl ether (150 ml). The mixture was stirred at room temperature for 16 hours and then hydrolized. The solvent was evaporated. Water was added. The mixture was extracted with DCM and decanted. The organic layer was dried, filtered and the solvent was evaporated till dryness, yielding 11 g (86.6%) of 6-(4-chlorophenyl)-4-(3-chlorophenyl)-8-methoxy-2(1H)-quinolinone (interm. 43).

f) A boron tribromide solution in DCM (1M; 95 ml) was added dropwise at 0° C. to a mixture of intermediate (43) (10 g) in DCM (100 ml). The mixture was stirred at room temperature overnight, then hydrolized, alkalized with $K_2CO_3$ (10%) and extracted with $CH_2Cl_2/CH_3OH$ 90/10. The organic layer was separated, dried, filtered and the solvent was evaporated till dryness. The product was used without further purification, yielding 9.6 g of 6-(4-chlorophenyl)-4-(3-chlorophenyl)-8-hydroxy-2(1H)-quinolinone (interm. 44)

g) A mixture of intermediate (44) (15 g), 1,2-dibromoethane (12.6 ml), potassium carbonate (20.2 g) and tricaprylylmethylammonium chloride (Aliquat 336) (1.6 ml) in ACN (120 ml) and DCM (180 ml) was stirred at 50° C. for 24 hours and then cooled to room temperature. Water was added. The mixture was decanted and extracted with DCM. The organic layer was separated, dried, filtered and the solvent was evaporated till dryness. The residue was purified by column chromatography over silica gel (eluent: $CH_2Cl_2$/EtOAc 95/5). Two pure fractions were collected and their solvents were evaporated, yielding 4.5 g (28.6%) of 9-(4-chlorophenyl)-7-(3-chlorophenyl)-2,3-dihydro-5H-pyrido[1,2,3-de]-1,4-benzoxazin-5-one (interm. 45).

h) Sodium borohydride ($NaBH_4$) (0.21 g) was added at 5° C. to a mixture of intermediate (45) (2.5 g) in methanol (30 ml) and THF (30 ml). The mixture was stirred at 5° C. for 30 minutes, then hydrolized, extracted with DCM and decanted. The organic layer was dried, filtered and the solvent was evaporated till dryness, yielding 2.3 g of (±)-7-(3-chlorophenyl)-9-[(4-chlorophenyl)hydroxymethyl]-2,3-dihydro-5H-pyridol[1,2,3-de]-1,4-benzoxazin-5-one (interm. 46).

i) A mixture of intermediate (46) (2.3 g) in thionylchloride (30 ml) was stirred at room temperature for 16 hours. The solvent was evaporated till dryness. The product was used without further purification, yielding 2.6 g of (±)-9-[chloro(4-chlorophenyl)methyl]-7-(3-chlorophenyl)-2,3-dihydro-5H-pyrido[1,2,3-de]-1,4-benzoxazin-5-one (intermediate 47).

In a similar way, (±)-8-[chloro(4-chlorophenyl)methyl]-6-(3-chlorophenyl)-2H,4H-oxazol[5,4,3-ij]quinolin-4-one (interm. 48) was also prepared.

EXAMPLE A.6

Intermediate (37) (23 g) and polyphosphoric acid (PPA) (120 g) were stirred at 140° C. for 24 hours. The mixture was poured out into ice water, filtered, washed with water, stirred in $NH_3$ (aq.), washed with water and extracted with DCM. The organic layer was separated, dried, filtered and the solvent was evaporated. The residue was purified by column chromatography over silica gel (eluent: DCM). The pure fractions were collected and the solvent was evaporated. Part of this fraction was crystallized from diethyl ether/2-propanone. The precipitate was filtered off and dried, yielding 0.6 g of (±)-6-(3-chlorophenyl)-1,2,5,6-tetrahydro-4H-pyrrolo[3,2,1-ij]quinolin-4-one (interm. 3).

EXAMPLE A.7 a) Pyridine (25 ml) was added to a mixture of 3,4-dihydro-2H-1,4-benzoxazine (17.8 g) in DCM (200 ml). The mixture was cooled on an ice bath and poured out into a mixture of m-chloro-cinnamoyl chloride (33 g) in DCM (100 ml). The mixture was stirred at room temperature overnight. Water was added and the mixture was decanted. The organic layer was dried, filtered and the solvent was evaporated till dryness, to give a residue which was purified by column chromatography over silica gel (eluent: cyclohexane/ethyl acetate 80/20) and recrystallisation from ACN/diethyl ether, yielding 26g (65.8%) of 4-[3-(3-chlorophenyl)-1-oxo-2-propen-1-yl]-2,3-dihydro-4H-1,4-benzoxazine (interm. 51).

b) $AlCl_3$ (7.2 g) was added to a mixture of intermediate (51) (5 g) in chlorobenzene (50 ml). The mixture was stirred and refluxed at 80° C. for 2 hours, then poured out on ice and extracted with DCM. The organic layer was separated, dried,-filtered and the solvent was evaporated. The residue was taken up in DCM, filtered off, washed with $CH_2Cl_2$/diethyl ether and dried, to givea residue which was purified by column chromatography over silica gel (eluent: $CH_2Cl_2$/$CH_3OH$ 99/1), yielding 3.4 g (62%) of (±)-7-(3-chlorophenyl)-2,3,6,7-tetrahydro-5H-pyrido[1,2,3-de]-1,4-benzoxazin-5-one (interm. 7).

EXAMPLE A.8 a) Butyllithium (1.6 M in hexanes, 22.4 ml) was added at −70° C. under nitrogen flow to a mixture of 1-methylimidazole (2.94 g) in THF (50 ml). The mixture was stirred at −70° C. for 30 minutes. Triethylsilyl chloride (6 ml) was added. The mixture was brought to room temperature and cooled to −70° C. Butyllithium (1.6 M in hexanes, 22.4 ml) was added. The mixture was stirred at −70° C. for 1 hour, then brought to −15° C. and cooled to −70° C. Intermediate 12 (3.8 g) was added portionwise. The mixture was brought to −10° C. Water was added and the mixture was extracted with ethyl acetate and a small amount of methanol. The organic layer was separated, dried, filtered and the solvent was evaporated. The residue was purified by column chromatography over silica gel (eluent: $CH_2Cl_2$/$CH_3OH$/$NH_4OH$ 95/5/0.2). The pure fractions were collected and the solvent was evaporated, yielding 4 g (88%) of (±)-4-(3-chlorophenyl)-6-[(4-chlorophenyl)hydroxy(1-methyl-1H-imidazol-5-yl)methyl]-8-methoxy-2(1H)-quinolinone (interm. 49).

b) A boron tribromide solution in DCM (1M; 27.6 ml) was added dropwise at 10° C. to a solution of intermediate (49) (2.8 g) in DCM (30 ml). The mixture was stirred at room temperature for 5 hours. Water was added slowly. The mixture was stirred at room temperature overnight. The precipitate was filtered off, washed with water and dried, yielding 2.9 g (100%) of (±)-4-(3-chlorophenyl)-6-[(4-chlorophenyl)hydroxy(1-methyl-1H-imidazol-5-yl)methyl]-8-hydroxy-2(1H)-quinolinone (interm. 50).

EXAMPLE A.9

Sodium borohydride (0.51 g) was added portionwise at room temperature to a solution of intermediate (23) (2.9 g) in methanol (20 ml) and THF (10 ml) and the mixture was stirred at room temperature for 1 hour. The mixture was poured into water and evaporated. Methanol was added, the mixture was extracted with DCM and decanted. The organic layer was dried, filtered and evaporated, yielding 2.9 g (100%) of (±)-7-(3-chlorophenyl)-9-[hydroxy(4-chlorophenyl)methyl]-2,3-dihydro-1H,5H-benzo[ij]quinolizin-5-one (interm. 52).

In a similar way, (±)-7-(3-chlorophenyl)-9-[hydroxy(4-chlorophenyl)methyl]-2,3,6,7-tetrahydro-1H,5H-benzo[ij]quinolizin-5-one (interm. 53) was synthesized.

EXAMPLE A.10

Methanesulfonyl chloride (1.6 ml) was added dropwise at room temperature to a solution of intermediate (52) (2.6 g) and triethylamine (4.1 ml) in DCM (30 ml) and the mixture was stirred at room temperature for 2 hours. The mixture was poured into water and decanted. The organic layer was dried, filtered and evaporated, yielding 3.4 g of (±)-7-(3-chlorophenyl)-9-[hydroxy(4-chlorophenyl)methyl]-2,3,6,7-tetrahydro-1H,5H-benzo[ij]quinolizin-5-one (interm. 54).

EXAMPLE A.11 a) 1,1'-Carbonyldiimidazole (41 g) was added portionwise at room temperature to a mixture of 2-amino-5-bromo-3-nitro-benzoic acid (55 g) in DCM (700 ml). The mixture was stirred at room temperature for 1 hour. N-methoxy-methanamine hydrochloride (24.6 g) was added. The mixture was stirred at room temperature overnight and hydrolized with water. The precipitate was filtered off and the filtrate was decanted. The organic layer was dried, filtered and the solvent was evaporated till dryness. The residue was purified by column chromatography over silica gel (eluent: $CH_2Cl_2$/ethyl acetate 98/2). The pure fractions were collected and the solvent was evaporated. The precipitate was taken up in HCl 3N (250 ml). The mixture was stirred at room temperature for 4 hours. The precipitate was filtered off, washed with water and dried, yielding 23 g of 2-amino-5-bromo-N-methoxy-N-methyl-3-nitrobenzamide (interm. 55, mp. 129° C.)

b) A mixture of 1-bromo-3-chlorophenyl (37.3 ml) in THF (300 ml) was added dropwise to a mixture of magnesium (7.7 g) in a small amount of THF, while the temperature was kept at 50° C.–60° C. The mixture was stirred at room temperature for 1 hour and cooled to 5° C. A mixture of intermediate (55) (30.7 g) in THF (300 ml) was added dropwise. The mixture was stirred at 5° C. for 15 minutes, hydrolized, extracted with ethyl acetate, filtered over celite and decanted. The organic layer was dried, filtered and the solvent was evaporated till dryness. The residue was purified by column chromatography over silica gel (eluent: $CH_2Cl_2$/cyclohexane 50/50). The pure fractions were collected and the solvent was evaporated, yielding 17.5 g (46.4%) of (2-amino-5-bromo-3-nitrophenyl)(3-chlorophenyl) methanone (interm. 56, mp. 134° C.).

c) $TiCl_3$ (15% in $H_2O$, 400 ml) was added at room temperature to a solution of intermediate (56) (16 g) in THF (230 ml). The mixture was stirred at room temperature overnight. Water was added and the mixture was extracted twice with DCM. The combined organic layer was washed with $K_2CO_3$ 10%, dried, filtered and the solvent was evaporated, yielding 18 g of (2,3-diamino-5-bromophenyl)(3-chlorophenyl)methanone (interm. 57)

d) A mixture of interm. (57) (18 g) and acetic acid anhydride (19 ml) in toluene (400 ml) was stirred and refluxed for 4 hours and then allowed to cool to room temperature. The precipitate was filtered off, washed with DIPE and dried, yielding 13.2 g (90%)of N,N'-[5-bromo-3-(3-chlorobenzoyl)-1,2-phenylene]diacetamide (interm. 58).

e) Potassium tert-butoxide (18 g) was added at room temperature to a mixture of interm. (58) (13.2 g) in DME (140 ml). The mixture was stirred at room temperature overnight. Water was added and the mixture was neutralized with HCl 3N. The precipitate was filtered off, washed with water and with DIPE and dried, yielding 10.75 g (86%) of N-[6-bromo-4-(3-chlorophenyl)-1,2-dihydro-2-oxo-8-quinolinyl]acetamide (interm. 59).

f) A mixture of interm. (59) (10.75 g), methyl iodide (3.57 ml) and $Ag_2CO_3$ (16.93 g) in DMF (150 ml) was stirred at 80° C. under $N_2$ flow for 90 minutes. The mixture was allowed to cool to room temperature. Water was added. The mixture was filtered over celite, washed with water and extracted with DCM. The organic layer was separated, dried, filtered and the solvent was evaporated, yielding 10.9 g (98%) of N-[6-bromo-4-(3-chlorophenyl)-2-methoxy-8-quinolinyl]acetamide (interm. 60).

g) Butyllithium (1.6 M in hexanes, 18.5 ml) was added dropwise at –70° C. under $N_2$ flow to a mixture of interm. (60) (5 g) in THF (70 ml). The mixture was stirred at –70° C. for 30 minutes, brought to –40° C. and cooled again to –70° C. (4-Chlorophenyl) (1-methyl-1H-imidazol-5-yl) methanone (6.5 g) was added. The mixture was allowed to warm to room temperature and then hydrolized. Ethyl acetate was added. The organic layer was separated, dried, filtered and the solvent was evaporated till dryness. The residue was purified by column chromatography over silica gel (eluent: $CH_2Cl_2$/$CH_3OH$/$NH_4OH$ 95/5/0. 1). The pure fraction was collected, evaporated, recrystallized from 2-propanone, ACN and DIPE, yielding 1.3 g (32.5%) of (±)-N-[4-(3-chlorophenyl)-6-[(4-chlorophenyl)hydroxy(1-methyl-1H-imidazol-5-yl)methyl]-2-methoxy-8-quinolinyl] acetamide (interm. 61, mp. 143° C.).

h) A mixture of interm. (61) (3 g) in HBr (48% in $H_2O$, 45 ml) and 1,4-dioxane (40 ml) was stirred at 80° C. for 3 hours. The mixture was cooled to room temperature, poured out on ice, saturated with $K_2CO_3$ solid and extracted with ethyl acetate. The organic layer was separated, dried, filtered, evaporated and purified by column chromatography over silica gel (eluent: $CH_2Cl_2$/$CH_3OH$/$NH_4OH$ 95/5/0.5). The pure fractions were collected and the solvent was evaporated. The residue was taken up in $CH_3OH$ and DIPE. The precipitate was filtered off and dried, yielding 0.4 g (55%) of (±)-8-amino-4-(3-chlorophenyl)-6-[(4-chlorophenyl)hydroxy(1-methyl-1H-imidazol-5-yl)methyl]-2(1H)-quinolinone(interm. 62).

Tables I-1 to I-2 list intermediates prepared according to one of the above Examples.

TABLE I-1

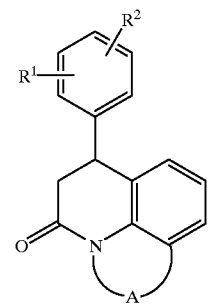

| Intm. No. | Ex. No. | —A— | $R^1$ | $R^2$ | Physical data |
|---|---|---|---|---|---|
| 1 | A.6 | —(CH$_2$)$_3$— | 3-Cl | H | — |
| 2 | A.6 | —(CH$_2$)$_2$— | 3-Br | H | — |
| 3 | A.6 | —(CH$_2$)$_2$— | 3-Cl | H | mp. 138° C. |
| 4 | A.6 | —(CH$_2$)$_2$— | 4-Cl | H | — |
| 5 | A.6 | —(CH$_2$)$_2$— | 3-Cl | 4-Cl | — |
| 6 | A.6 | —(CH$_2$)$_2$— | 3-CH$_3$ | H | — |
| 7 | A.7 | —(CH$_2$*)$_2$—O— | 3-Cl | H | — |

*the CH$_2$ moiety is linked to the nitrogen atom of the 2-quinolinone moiety

TABLE I-2

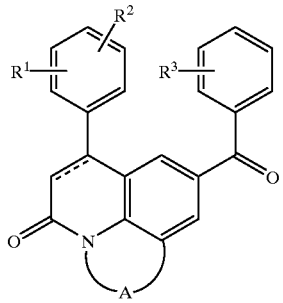

| Intm. No. | Ex. No. | ----- | —A— | R¹ | R² | R³ | Physical data |
|---|---|---|---|---|---|---|---|
| 8 | A.2 | single | —(CH₂)₃— | 3-Cl | H | 4-Cl | mp. 176° C. |
| 9 | A.2 | single | —(CH₂)₂— | H | H | 4-Cl | — |
| 10 | A.2 | single | —(CH₂)₂— | 3-Br | H | 4-Cl | — |
| 11 | A.2 | single | —(CH₂)₂— | 3-Cl | H | 4-Cl | mp. 140° C. |
| 12 | A.2 | single | —(CH₂)₂— | 3-Cl | H | 4-F | — |
| 13 | A.2 | single | —(CH₂)₂— | 3-Cl | H | 3-Cl | — |
| 14 | A.2 | single | —(CH₂)₂— | 3-Cl | 4-Cl | 4-Cl | — |
| 15 | A.2 | single | —(CH₂)₂— | 3-Cl | H | H | — |
| 16 | A.2 | single | —(CH₂)₂— | 3-Cl | H | 4-CH₃ | — |
| 17 | A.2 | single | —(CH₂)₂— | 3-Cl | H | 2-Cl | — |
| 18 | A.2 | single | —(CH₂)₂— | 3-Cl | H | 4-OCH₃ | — |
| 19 | A.2 | single | —(CH₂)₂— | 4-Cl | H | 4-Cl | — |
| 20 | A.2 | single | —(CH₂)₂— | 3-CH₃ | H | 4-Cl | — |
| 21 | A.4 | double | —(CH₂)₂— | H | H | 4-Cl | — |
| 22 | A.4 | double | —(CH₂)₂— | 3-Br | H | 4-Cl | — |
| 23 | A.4 | double | —(CH₂)₃— | 3-Cl | H | 4-Cl | mp. 194° C. |
| 24 | A.3 | double | —(CH₂)₂— | 3-Cl | H | 4-Cl | mp. 191° C. |
| 25 | A.3 | double | —CH=CH— | 3-Cl | H | 4-Cl | — |
| 26 | A.5 | double | —(CH₂*)₂—O— | 3-Cl | H | 4-Cl | mp. 135° C. |
| 27 | A.5 | double | —CH₂*—O— | 3-Cl | H | 4-Cl | mp. 154° C. |
| 28 | A.4 | double | —(CH₂)₂— | 3-Cl | H | 4-F | — |
| 29 | A.4 | double | —(CH₂)₂— | 3-Cl | H | 3-Cl | — |
| 30 | A.4 | double | —(CH₂)₂— | 3-Cl | 4-Cl | 4-Cl | — |
| 31 | A.4 | double | —(CH₂)₂— | 3-Cl | H | H | — |
| 32 | A.4 | double | —(CH₂)₂— | 3-Cl | H | 4-CH₃ | — |
| 33 | A.4 | double | —(CH₂)₂— | 3-Cl | H | 2-Cl | — |
| 34 | A.4 | double | —(CH₂)₂— | 3-Cl | H | 4-OCH₃ | — |
| 35 | A.4 | double | —(CH₂)₂— | 4-Cl | H | 4-Cl | — |
| 36 | A.4 | double | —(CH₂)₂— | 3-CH₃ | H | 4-Cl | — |

*the CH₂ moiety is linked to the nitrogen atom of the 2-quinolinone moiety

B. Preparation of the Final Compounds

EXAMPLE B.1

A solution of 1-methylimidazole (4.55 ml) in THF (200 ml) was cooled to −70° C. Butyllithium (1.6 M in hexanes, 35.9 ml) was added and the mixture was stirred at −70° C. for 30 minutes. Triethylsilyl chloride (10.4 ml) was added and the mixture was allowed to warm to room temperature slowly. The mixture was cooled to −70° C. and butyllithium (1.6 M in hexanes 35.9 ml) was added dropwise. The mixture was stirred at −70° C. for 1 hour and was then allowed to warm to −15° C. The bath was removed and the mixture was cooled to −70° C. Intermediate (24) (20 g) was added and the mixture was stirred at −70° C. for 30 minutes. The mixture was hydrolyzed and extracted with ethyl acetate. The organic layer was separated, dried, filtered and the solvent was evaporated. The residue was purified by column chromatograph (eluent: CH₂Cl₂/CH₃OH/NH₄OH 97/3/0.1), yielding 24 g of (±)-6-(3-chlorophenyl)-8-[(4-chlorophenyl)hydroxy(1-methyl-1H-imidazol-5-yl)methyl]-1,2-dihydro-4H-pyrrolo[3,2,1-ij]quinolin-4-one (comp. 5, mp. 213.6° C.).

EXAMPLE B.2

A mixture of compound 1 (2.5 g) in formamide (10 ml) and acetic acid (20 ml) was stirred at 160° C. for 4 hours. The mixture was poured out on ice, basified with an aqueous ammonia solution and extracted with DCM. The organic layer was separated, dried, filtered and the solvent was evaporated. The residue was purified by column chromatography over silica gel (eluent: CH₂Cl₂/CH₃OH/NH₄OH 97/3/0.1). The pure fractions were collected and the solvent was evaporated. The residue was taken up in 2-propanone/DIPE. The precipitate was filtered off and dried, yielding 1 g (41%) of (±)-6-(3-chlorophenyl)-8-[(4-chlorophenyl)(1-methyl-1H-imidazol-5-yl)methyl]-1,2-dihydro-4H-pyrrolo[3,2,1-ij]quinolin-4-one monohydrate (comp. 6, mp. 147.0° C.).

EXAMPLE B.3

A mixture of compound 5 (2 g) in thionyl chloride (8 ml) was stirred at room temperature overnight. The solvent was evaporated till dryness. The product was used without further purification, yielding 2.07 g (100%) of (±)-8-[chloro(4-chlorophenyl)(1-methyl-1H-imidazol-5-yl)methyl]-6-(3-chlorophenyl)-1,2-dihydro-4H-pyrrolo[3,2,1-ij]quinolin-4-one monohydrochloride (comp. 7).

EXAMPLE B.4

A mixture of compound 7 (2.07 g) in THF (15 ml) was poured out into an aqueous ammonia solution (40 ml) at room temperature. The mixture was stirred at room temperature for 4 hours, then extracted with DCM and decanted. The organic layer was dried, filtered and the solvent was evaporated. The residue was purified by column chromatography over silica gel (eluent:toluene/2-propanol/NH$_4$OH 50/50/1). The pure fractions were collected and the solvent was evaporated. The residue was recrystallized from CH$_2$Cl$_2$/diethyl ether. The precipitate was filtered off and dried, yielding 0.65 g (±)-8-[amino(4-chlorophenyl)(1-methyl-1H-imidazol-5-yl)methyl]-6-(3-chlorophenyl)-1,2-dihydro-4H-pyrrolo[3,2,1-ij]quinolin-4-one (comp. 8).

EXAMPLE B.5

Compound 8 (12.4 g) was separated and purified by chiral column chromatography over Chiracel OD (eluent: 100% CH$_3$OH). Two pure fraction groups were collected. The solvent of the first fraction group was evaporated. The residue was crystallized from 2-propanol (200 ml) and DIPE (200 ml). The precipitate was filtered off and dried, yielding 4.4 g of (A)-8-[amino(4-chlorophenyl)(1-methyl-1H-imidazol-5-yl)methyl]-6-(3-chlorophenyl)-1,2-dihydro-4H-pyrrolo[3,2,1-ij]quinolin-4-on (compound9; $[\alpha]_D^{20}$=−27.94° (c=9.1 mg/ml in methanol)).

The solvent of the second fraction group was evaporated. The residue was crystallized from 2-propanol (250 ml) and DIPE (350 ml). The precipitate was filtered off and dried, yielding: 4.1 g of (B)-8-[amino(4-chlorophenyl)(1-methyl-1H-imidazol-5-yl)methyl]-6-(3-chlorophenyl)-1,2-dihydro-4H-pyrrolo[3,2,1-ij]quinolin-4-on (compound 10; $[\alpha]_D^{20}$=+28.21° (c=9 mg/ml in methanol)).

EXAMPLE B.6

A mixture of intermediate (50) (2.7 g), dibromomethane (3 ml) and potassium carbonate (2.8 g) in DMF (90 ml) was stirred at 80° C. for 3 hours. Water was added. The mixture was filtered over celite, washed with water and extracted with DCM. The organic layer was separated, dried, filtered and the solvent was evaporated. The residue was purified by column chromatography over silica gel (eluent: CH$_2$Cl$_2$/CH$_3$OH/NH$_4$OH96/4/0.2). The pure fraction were collected and the solvent was evaporated. The residue was crystallized from 2-propanone and diethyl ether. The precipitate was filtered off and dried, yielding 0.86 g (31%) of (±)-6-(3-chlorophenyl)-8-[(4-chlorophenyl)hydroxy(1-methyl-1H-imidazol-5-yl)methyl]-2H,4H-oxazolo[5,4,3-ij]quinolin-4-one (comp. 15).

EXAMPLE B.7

A mixture of compound 6 (1.2 g) and phosphorus sulfide (2.4 g) in pyridine (30 ml) was stirred and refluxed for 6 hours and then poured out into water. The precipitate was filtered off, rinced abundantly with water, taken up in DCM, dried, filtered and the solvent was evaporated till dryness. The residue was purified by column chromatography over silica gel (eluent: CH$_2$Cl$_2$/CH$_3$OH/NH$_4$OH 98/2/0.1). The pure fractions were collected and the solvent was evaporated. The residue was crystallized from ACN and DIPE. The precipitate was filtered off and dried, yielding 0.36 g (29.2%) of (±)-6-(3-chlorophenyl)-8-[(4-chlorophenyl)(1-methyl-1H-imidazol-5-yl)methyl]-1,2-dihydro-4H-pyrrolo[3,2,1-ij]quinoline-4-thione (comp. 27).

EXAMPLE B.8

A mixture of interm. (62) (1.8 g) and ethyl acetimidate (0.9 g) in methanol (40 ml) was stirred and refluxed for 4 hours. The solvent was evaporated till dryness. The residue was taken up in DCM and K$_2$CO$_3$ (10% in H$_2$O). The organic layer was separated, dried, filtered and the solvent was evaporated. The residue was purified by column chromatography over silica gel (eluent: CH$_2$Cl$_2$/CH$_3$OH/NH$_4$OH 95/5/0.5). The pure fractions were collected and the solvent was evaporated. The residue was crystallized from DIPE. The precipitate was filtered off and dried, yielding 0.4 g (21.2%) of (±)-6-(3-chlorophenyl)-8-[(4-chlorophenyl)hydroxy(1-methyl-1H-imidazol-5-yl)methyl]-2-methyl-4H-imidazo[4,5,1-ij]quinolin-4-one (comp. 30, mp. 170° C.).

In a similar way, (±)-6-(3-chlorophenyl)-8-[(4-chlorophenyl)hydroxy(1-methyl-1H-imidazol-5-yl)methyl]-2-phenyl-4H-imidazo[4,5,1-ij]quinolin-4-one (comp. 31) was also prepared.

EXAMPLE B.9

A mixture of interm. (62) (2.1 g) and 1,1'-carbonyldiimidazole (4.1) in THF (60 ml) was stirred and refluxed for 3 hours. The mixture was poured out into water and extracted with DCM. The organic layer was separated, washed with water, dried, filtered and the solvent was evaporated till dryness. The residue was purified by column chromatography over silica gel (eluent: CH$_2$Cl$_2$/CH$_3$OH/NH$_4$OH 90/10/0.5). The pure fractions were collected and the solvent was evaporated. The residue was crystallized from CH$_3$OH and DIPE. The precipitate was filtered off and dried, yielding 0.7 g (31.8%) of (±)-6-(3-chlorophenyl)-8-[(4-chlorophenyl)hydroxy(1-methyl-1H-imidzol-5-yl)methyl]-4H-imidazo[4,5,1-ij]quinoline-2,4(1H)-dione (comp. 34, mp. 256° C.).

EXAMPLE B.10

A mixture of interm. (62)(2.1 g) in water (21 ml) and sulfuric acid (36 N, 42 ml) was cooled to 5° C. on an ice bath. NaNO$_2$ (3.6 ml; solution 80 g/100 ml) was added dropwise while the temperature was kept at 5° C. The mixture was stirred for 1 hour on an ice bath, poured out into ice water, alkalized with a concentrated NH$_4$OH solution and extracted with DCM. The organic layer was separated, dried, filtered and the solvent was evaporated. The residue was purified by column chromatography over silica gel (eluent: CH$_2$Cl$_2$/CH$_3$OH/NH$_4$OH 97.5/2.5/0.1). The pure fractions were collected and the solvent was evaporated. The residue was crystallized from 2-propanone and DIPE. The precipitate was filtered off and dried, yielding 0.35 g (16.3%) of (±)-6-(3-chlorophenyl)-8-[(4-chlorophenyl)hydroxy(1-methyl-1H-imidazol-5-yl)methyl]-4H-1,2,3-triazolo[4,5,1-ij]quinolin-4-one (comp. 35, mp. 226° C.).

EXAMPLE B.11

A mixture of intermediate (54) (3.4 g) and imidazole (2.01 g) in ACN (40 ml) was stirred and refluxed for 3 hours. The mixture was evaporated and the residue was taken up in DCM. The organic layer was washed with water, dried, filtered off and evaporated. The residue was purified by colymn chromatography over silica gel (eluent: CH$_2$Cl$_2$/CH$_3$OH/NH$_4$OH 97/3/0.1). The pure fractions were collected and evaporated. Crystallisation from ethyl acetate and DIPE yielded 1.9 g (65%) (±)-7-(3-chlorophenyl)-9-[(4-chlorophenyl)-1H-imidazol-1-ylmethyl]-2,3-dihydro-1H,5H-benzo[ij]quinolizin-5-one (comp. 36, mp. 195.2° C.).

EXAMPLE B.12

1,1'-Carbonyldiimidazole (4 g) was added at room temperature to a solution of intermediate (53) (5.4 g) in THF (70 ml) and the mixture was stirred at room temperature for 16 hours. Water was added and the mixture was extracted with DCM. The organic layer was dried, filtered and evaporated. The residue was purified by column chromatography over silica gel (eluent: CH$_2$Cl$_2$/CH$_3$OH/NH$_4$OH 97.5/2.5/0.1).

The pure fractions were collected and evaporated. The residue was purified further by column chromatography over silica gel (eluent: cyclohexane/2-propanol/NH$_4$OH 80/20/0.1). The pure fractions were collected and evaporated. The residue was taken up in diethyl ether and filtered off, yielding 1.3 g (22%) of (±)-7-(3-chlorophenyl)-9-[(4-chlorophenyl)-1H-imidazol-1-ylmethyl]-2,3,6,7-tetrahydro-1H,5H-benzo[ij]quinolizin-5-one (comp. 37, mp. 93.6° C.).

EXAMPLE B.13

A mixture of intermediate (48) (2.3 g) and imidazole (1.8 g) in ACN (50 ml) was stirred and refluxed for 4 hours. The solvent was evaporated till dryness. The residue was taken up in DCM, washed with water and decanted. The organic layer was dried, filtered and the solvent was evaporated till dryness. The residue was purified by column chromatography over silica gel (eluent: CH$_2$Cl$_2$/CH$_3$OH/NH$_4$OH 98/2/0.1). The pure fractions were collected and the solvent was evaporated. The residue was crystallized from ACN and DIPE. The precipitate was filtered off and dried, yielding 1.3 g of (±)-6-(3-chlorophenyl)-8-[(4chlorophenyl)-1H-imidazol-1ylmethyl]-2H,4H-oxazolo[5,4,3-ij]quinolin-4-one (comp. 52).

EXAMPLE B.14

Phosphorus sulfide (6 g) was added to a mixture of compound 38 (3 g) in pyridine (40 ml). The mixture was stirred and refluxed for 6 hours. Ice water was added. The precipitate was filtered off, washed with water and taken up in DCM. The organic layer was separated, dried, filtered and the solvent was evaporated till dryness. The residue was purified by column chromatography over silica gel (eluent: CH$_2$Cl$_2$/CH$_3$OH 98.5/1.5). The pure fractions were collected and the solvent was evaporated. The residue was crystallized from ACN and DIPE. The precipitate was filtered off and dried, yielding 1.1 g of (±)-6-(3-chlorophenyl)-8-[(4-chlorophenyl)-1H-imidazol-1-ylmethyl]-1,2-dihydro-4H-pyrrolo[3,2,1-ij]quinoline-4-thione (comp. 50).

Tables F-1 and F-3 list the compounds that were prepared according to one of the above Examples.

TABLE F-1

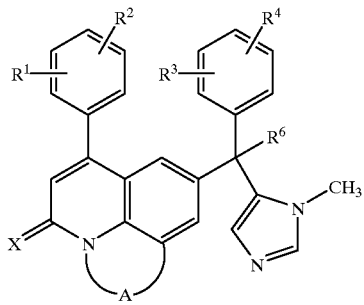

| Co. No. | Ex. No. | X | —A— | R$^1$ | R$^2$ | R$^3$ | R$^4$ | R$^6$ | Physical data |
|---|---|---|---|---|---|---|---|---|---|
| 1 | B.1 | O | —(CH$_2$)$_2$— | H | H | 4-Cl | H | OH | mp. 240° C. |
| 2 | B.3 | O | —(CH$_2$)$_2$— | H | H | 4-Cl | H | Cl | (2) |
| 3 | B.4 | O | —(CH$_2$)$_2$— | H | H | 4-Cl | H | NH$_2$ | mp. 218° C. |
| 4 | B.1 | O | —(CH$_2$)$_2$— | 3-Br | H | 4-Cl | H | OH | mp. 210° C. |
| 5 | B.1 | O | —(CH$_2$)$_2$— | 3-Cl | H | 4-Cl | H | OH | mp. 213.6° C. |
| 6 | B.2 | O | —(CH$_2$)$_2$— | 3-Cl | H | 4-Cl | H | H | mp. 147.0° C.; (1) |
| 7 | B.3 | O | —(CH$_2$)$_2$— | 3-Cl | H | 4-Cl | H | Cl | (2) |
| 8 | B.4 | O | —(CH$_2$)$_2$— | 3-Cl | H | 4-Cl | H | NH$_2$ | mp. 165° C. |
| 9 | B.5 | O | —(CH$_2$)$_2$— | 3-Cl | H | 4-Cl | H | NH$_2$ | (A); [α]$_D^{20}$ = −27.94° |
| 10 | B.5 | O | —(CH$_2$)$_2$— | 3-Cl | H | 4-Cl | H | NH$_2$ | (B); [α]$_D^{20}$ = +28.21° |
| 11 | B.1 | O | —(CH$_2$)$_3$— | 3-Cl | H | 4-Cl | H | OH | mp. 210° C.(dec.) |
| 12 | B.1 | O | —(CH$_2$)$_3$— | 3-Cl | H | 4-Cl | H | OH | mp. 232° C.; (2) |
| 13 | B.3 | O | —(CH$_2$)$_3$— | 3-Cl | H | 4-Cl | H | Cl | (2) |
| 14 | B.4 | O | —(CH$_2$)$_3$— | 3-Cl | H | 4-Cl | H | NH$_2$ | mp. 190° C. |
| 15 | B.6 | O | —CH$_2$*—O— | 3-Cl | H | 4-Cl | H | OH | mp. 196° C. |
| 16 | B.3 | O | —(CH$_2$)$_2$—O— | 4-Cl | H | 4-Cl | H | Cl | (2) |
| 17 | B.1 | O | —(CH$_2$*)$_2$—O— | 3-Cl | H | 4-Cl | H | OH | mp. 252° C. |
| 18 | B.4 | O | —(CH$_2$*)$_2$—O— | 3-Cl | H | 4-Cl | H | NH$_2$ | mp. 210° C. |
| 19 | B.1 | O | —(CH$_2$)$_2$— | 3-Cl | H | 4-F | H | OH | mp. 224° C. |
| 20 | B.3 | O | —(CH$_2$)$_2$— | 3-Cl | H | 4-F | H | Cl | (2) |
| 21 | B.4 | O | —(CH$_2$)$_2$— | 3-Cl | H | 4-F | H | NH$_2$ | mp. 235° C. |
| 22 | B.1 | O | —(CH$_2$)$_2$— | 3-Cl | H | 3-Cl | H | OH | mp. 220° C. |
| 23 | B.1 | O | —(CH$_2$)$_2$— | 3-Cl | H | H | H | OH | mp. 260° C. |
| 24 | B.1 | O | —(CH$_2$)$_2$— | 3-Cl | H | 4-CH$_3$ | H | OH | mp. 245° C. |
| 25 | B.1 | O | —(CH$_2$)$_2$— | 3-Cl | H | 2-Cl | H | OH | mp. 210° C.; (1) |
| 26 | B.1 | O | —(CH$_2$)$_2$— | 3-CH$_3$ | H | 4-Cl | H | OH | mp. 242° C. |
| 27 | B.7 | S | —(CH$_2$)$_2$— | 3-Cl | H | 4-Cl | H | H | mp. 138° C. |
| 30 | B.8 | O | —CH(CH$_3$)=N— | 3-Cl | H | 4-Cl | H | OH | mp. 170° C. |
| 31 | B.6 | O | —CH(C$_6$H$_5$)=N— | 3-Cl | H | 4-Cl | H | OH | mp. 176° C. |
| 32 | B.3 | O | —CH(C$_6$H$_5$)=N— | 3-Cl | H | 4-Cl | H | Cl | (1) |
| 33 | B.4 | O | —CH(C$_6$H$_5$)=N— | 3-Cl | H | 4-Cl | H | NH$_2$ | mp. 215° C. |

TABLE F-1-continued

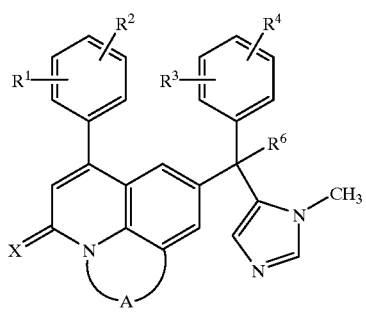

| Co. No. | Ex. No. | X | —A— | R¹ | R² | R³ | R⁴ | R⁶ | Physical data |
|---|---|---|---|---|---|---|---|---|---|
| 34 | B.9 | O | —CO—NH— | 3-Cl | H | 4-Cl | H | OH | mp. 256° C. |
| 35 | B.10 | O | —N=N— | 3-Cl | H | 4-Cl | H | OH | mp. 226° C. |

*the CH₂ moiety is linked to the nitrogen atom of the 2-quinolinone moiety
(1) hydrate (1:1)
(2) hydrochloride (1:1)

TABLE F-2

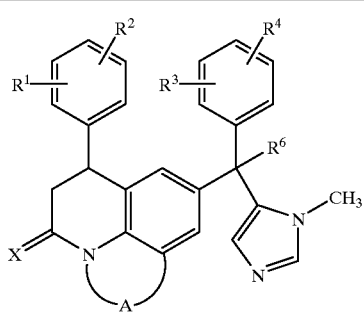

| Co. No. | Ex. No. | X | —A— | R¹ | R² | R³ | R⁴ | R⁶ | Physical data |
|---|---|---|---|---|---|---|---|---|---|
| 28 | B.1 | O | —(CH₂)₂— | 3-Cl | H | 4-Cl | H | OH | mp. 248° C. |
| 29 | B.1 | O | —(CH₂)₃— | 3-Cl | H | 4-Cl | H | OH | (3); mp. 154° C. |

(3) ethanedioate (1:1) hydrate (1:1)

TABLE F-3

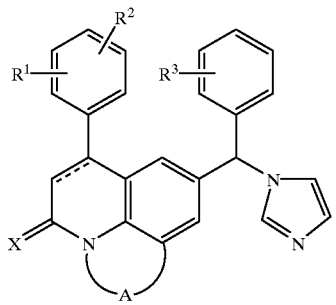

| Co. No. | Ex. No. | ----- | —A— | X | R¹ | R² | R³ | Physical data |
|---|---|---|---|---|---|---|---|---|
| 36 | B.11 | double | —(CH₂)₃— | O | 3-Cl | H | 4-Cl | mp. 195.2° C. |
| 37 | B.12 | single | —(CH₂)₃— | O | 3-Cl | H | 4-Cl | mp. 93.6° C. |
| 38 | B.11 | double | —(CH₂)₂— | O | 3-Cl | H | 4-Cl | mp. 204.1° C. |
| 39 | B.13 | double | —(CH₂)₂— | O | 3-Cl | H | H | mp. 200° C. |

TABLE F-3-continued

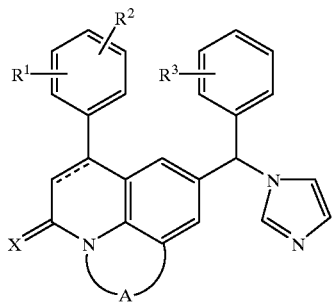

| Co. No. | Ex. No. | —A— | X | R¹ | R² | R³ | Physical data |
|---|---|---|---|---|---|---|---|
| 40 | B.13 | double | —(CH$_2$)$_2$— | O | 3-Cl | H | 2-Cl | mp. 216° C. |
| 41 | B.13 | double | —(CH$_2$)$_2$— | O | 3-Cl | H | 3-Cl | mp. 180° C. |
| 42 | B.13 | double | —(CH$_2$)$_2$— | O | 3-Cl | H | 4-F | mp. 210° C. |
| 43 | B.13 | double | —(CH$_2$)$_2$— | O | 3-Cl | H | 4-CH$_3$ | mp. 210° C. |
| 44 | B.13 | double | —(CH$_2$)$_2$— | O | 3-Cl | H | 4-OCH$_3$ | mp. 120° C. |
| 45 | B.13 | double | —(CH$_2$)$_2$— | O | 3-Cl | 4-Cl | 4-Cl | mp. 210° C. |
| 46 | B.13 | double | —(CH$_2$)$_2$— | O | 4-Cl | H | 4-Cl | mp. 190° C.; (1) |
| 47 | B.13 | double | —(CH$_2$)$_2$— | O | 3-CH$_3$ | H | 4-Cl | mp. 200° C. |
| 48 | B.13 | double | —(CH$_2$)$_2$— | O | 3-Br | H | 4-Cl | mp. 196° C. |
| 49 | B.13 | double | —(CH$_2$)$_2$— | O | H | H | 4-Cl | mp. 184° C.; (1) |
| 50 | B.14 | double | —(CH$_2$)$_2$— | S | 3-Cl | H | 4-Cl | mp. 253° C. |
| 51 | B.11 | double | —CH=CH— | O | 3-Cl | H | 4-Cl | mp. 104° C. |
| 52 | B.13 | double | —(CH$_2$*)—O— | O | 3-Cl | H | 4-Cl | mp. 208° C. |
| 53 | B.13 | double | —(CH$_2$*)$_2$—O— | O | 3-Cl | H | 4-Cl | mp. 180° C. |

*the CH$_2$ moiety is linked to the nitrogen atom of the 2-quinolinone moiety
(1) ethanedioate (2:3) salt C. Pharmacological Example EXAMPLE C.1
"In Vitro Assay for Inhibition of Farnesyl Protein Transferase"

Human farnesyl protein transferase was prepared essentially as described (Y. Reiss et al., Methods: A Companion to Methods in Enzymology, vol. 1, 241–245, 1990). Kirsten virus transformed human osteosarcoma (KHOS) cells (American Type Culture Collection, Rockville, Md., USA) grown as solid tumors in nude mice or grown as monolayer cell cultures were used as a source of human enzyme. Briefly, cells or tumors were homogenized in buffer containing 50 mM Tris, 1 mM EDTA, 1 mM EGTA and 0.2 mM phenylmethylsulfonylfluoride (pH 7.5). The homogenates were centrifuged 28,000×g for 60 min and the supernatants collected. A 30–50% ammonium sulfate fraction was prepared, and the resulting precipitate was resuspended in a small (10 to 20 ml) volume of dialysis buffer containing 20 mM Tris, 1 mM dithiothreitol and 20 μM ZnCl$_2$. The ammonium sulfate fraction was dialyzed overnight against two changes of the same buffer. The dialyzed material was applied to a 10×1 cm Q Fast Flow Sepharose (Pharmacia LKB Biotechnology Inc., Piscataway, N.J., USA) which had been preequilibrated with 100 ml of dialysis buffer supplemented with 0.05 M NaCl. The column was washed with an additional 50 ml of dialysis buffer plus 0.05 M NaCl followed by a gradient from 0.05 M to 0.25 M NaCl prepared in dialysis buffer. The enzyme activity was eluted with a linear gradient of 0.25 to 1.0 M NaCl prepared in the dialysis buffer. Fractions containing 4 to 5 ml volumes of column eluate were collected and analyzed for farnesyl protein transferase activity. Fractions with enzyme activity were pooled and supplemented with 100 μM ZnCl$_2$. Enzyme samples were stored frozen at −70° C.

The activity of farnesyl protein transferase was measured using the Farnesyl Transferase [$^3$H] Scintillation Proximity Assay (Amersham International plc., England) under the conditions specified by the manufacturer. To assay for inhibitors of the enzyme, 0.20 μCi of the [$^3$H]-farnesylpyrophosphate substrate and the biotinylated lamin B peptide substrate (biotin-YRASNRSCAIM) were mixed with test compounds in a reaction buffer consisting of 50 mM HEPES, 30 mM MgCl$_2$, 20 mM KCl, 5 mM dithiothreitol, 0.01% Triton X-100. Test compounds were delivered in a 10 μl volume of dimethylsulfoxide (DMSO) to achieve concentrations of 1 and 10 μg/ml in a final volume of 100 μl. The reaction mixture was warmed to 37° C. The enzyme reaction was started by adding 20 μl of diluted human farnesyl protein transferase. Sufficient enzyme preparation was added to produce between 4000 to 15000 cpm of reaction product during the 60 min of reaction incubation at 37° C. Reactions were terminated by the addition of STOP/scintillation proximity bead reagent (Amersham). The reaction product [$^3$H]-farnesyl-(Cys)-biotin lamin B peptide was captured on the streptavidin linked scintillation proximity bead. The amount of [$^3$H]-farnesyl-(Cys)-biotin lamin B peptide synthesized in the presence or absence of test compounds was quantified as cpm by counting on a Wallac Model 1480 Microbeta Liquid Scintillation Counter. The cpm of product was considered to be farnesyl protein transferase activity. The protein farnesyl transferase activity observed in the presence of test compound was normalized to farnesyl transferase activity in the presence of 10% DMSO and expressed as per cent inhibition. In separate studies, some test compounds exhibiting 50% or greater inhibition of farnesyl protein transferase activity were evaluated for concentration-dependent inhibition of enzyme activity. The effects of test compounds in these studies were calculated as IC$_{50}$ (concentration of test compound producing 50% inhibition of enzyme activity) using the LGIC50 computer program written by the Science Information Division of R. W. Johnson Pharmaceutical Research Institute (Spring House, Pa., USA) on a VAX computer. Compound 36 was found to have a $IC_{50}$ of 21 nM and compound 38 to have a $IC_{50}$ of 15 nM.

EXAMPLE C.2
"Ras-Transformed Cell Phenotype Reversion Assay"

Insertion of activated oncogenes such as the mutant ras gene into mouse NIH 3T3 cells converts the cells to a transformed phenotype. The cells become tumorigenic, display anchorage independent growth in semi-solid medium and lose contact inhibition. Loss of contact inhibition produces cell cultures which no longer form uniform monolayers. Rather, the cells pile up into multicellular nodules and grow to very high saturation densities in plastic tissue culture dishes. Agents such as protein farnesyl transferase inhibitors which revert the ras transformed phenotype restore the uniform monolayer growth pattern to cells in culture. This reversion is easily monitored by counting the number of cells in tissue culture plates. Transformed cells will achieve higher cell numbers than cells which have reverted to an untransformed phenotype. Compounds which revert the transformed phenotype should produce antitumor effects in tumors bearing ras gene mutations.

Method

Compounds are screened in tissue culture in NIH 3T3 cells transformed by the T24 activated human H-ras gene. Cells are seeded at an initial density of 200,000 cells per well (9.6 cm² surface area) in six-well cluster tissue culture plates. Test compounds are immediately added to 3.0 ml cell growth medium in a 3.0 µl volume of DMSO, with a final concentration of DMSO in the cell growth medium of 0.1%. The test compounds are run at concentrations of 5, 10, 50, 100, and 500 nM along with a DMSO treated vehicle control. (In case a high activity is observed at 5 nM, the test compound is tested at even lower concentrations.) The cells are allowed to proliferate for 72 hours. Then the cells are detached in 1.0 ml trypsin-EDTA cell dissociation medium and counted on a Coulter particle counter.

Measurements

Cell numbers expressed as cells per well are measured using a Coulter Particle Counter.

All cell counts were corrected for the initial cell input density by subtracting 200,000.

Control cell counts=[cell counts from cells incubated with DMSO vehicle−200,000]

Test compound cell counts =

[cell counts from cells incubated with test compound − 200,000].

$$\text{Test compound \% inhibition} = \left[1 - \frac{\text{test compound cell counts}}{\text{control cell counts}}\right] \times 100\%.$$

$IC_{50}$ (i.e. the test compound concentration required to inhibit enzyme activity by 50%) is calculated if sufficient data are available, summarized in table C.2.

TABLE C.2

| Co. No. | $IC_{50}$ (nM) |
|---|---|
| 1 | 142 |
| 3 | 51 |
| 4 | 50 |
| 5 | 7.8 |
| 6 | 32 |
| 8 | 6.4 |
| 10 | 3.2 |
| 12 | 66 |
| 14 | 7.3 |
| 15 | 48 |

TABLE C.2-continued

| Co. No. | $IC_{50}$ (nM) |
|---|---|
| 17 | 63 |
| 18 | >500 |
| 19 | 240 |
| 21 | 18 |
| 22 | 352 |
| 23 | 442 |
| 24 | 12 |
| 25 | 37 |
| 26 | 21 |
| 27 | 37.1 |
| 28 | 100 |
| 29 | 184 |
| 30 | 373 |
| 31 | >500 |
| 33 | 73.1 |
| 34 | >500 |
| 35 | >500 |
| 40 | >500 |
| 41 | >500 |
| 44 | 353 |
| 45 | >500 |
| 48 | >500 |
| 49 | >500 |
| 51 | >500 |
| 53 | >500 |

EXAMPLE C.3

"Farnesyl Protein Transferase Inhibitor Secondary Tumor Model"

The enzyme farnesyl protein transferase catalyzes the covalent attachment of a farnesyl moiety derived from farnesyl pyrophosphate to the oncogene product $p21^{ras}$. This directs $p21^{ras}$ to attach to plasma membranes. Once attached to plasma membranes, mutant or oncogenic forms of $p21^{ras}$ will provide a signal for the transformation and uncontrolled growth of malignant tumor cells. Therefore, inhibitors of protein farnesyltransferase will prevent the membrane attachment of $p21^{ras}$ and inhibit growth of ras-transformed tumors.

Nude mice are inoculated with 1×10⁶ of T24 activated human H-ras gene transformed NIH 3T3 fibroblast cells (T24 cells), subcutaneously in the inguinal region. After three days to allow tumors to become established, treatment with test compounds is begun via the oral route. The test compounds are dissolved in a 20% β-cyclodextrin in 0.1 N HCl solution and administered orally as 0.1 ml of compound solution per 10 g mouse body weight. Routinely used doses are 6.25, 12.5 and 25 mg/kg. Body weights and tumor sizes are monitored during the ensuing 15 days of treatment. At the end of treatment, animals are sacrificed and tumors are weighed.

The "mean vehicle treated tumor weight" is defined as the mean tumor weight from 10 to 15 mice treated with the test compound.

The "mean tumor weight" is defined as the mean tumor weight from 10 to 15 mice not treated with the test compound.

$$\% \text{ Reduction final tumor weight} = \left[1 - \frac{\text{mean tumor weight}}{\text{mean vehicle treated tumor weight}}\right] \times 100\%.$$

TABLE C.3

| Co. No. | Dose | % reduction final tumor weight |
|---|---|---|
| 8 | 6.25 mg/kg bid, po | 41% |
|  | 12.25 mg/kg bid, po | 44% |
|  | 25 mg/kg bid, po | 49% |

What is claimed is:

1. A compound of formula (I)

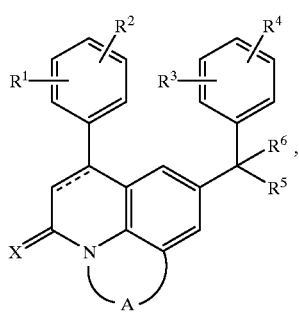

a pharmaceutically acceptable acid addition salt or a stereochemically isomeric form thereof, wherein
the dotted line represents an optional bond;
X is oxygen or sulfur;
—A— is a bivalent radical of formula

| —CH=CH— | (a-1), | —CH$_2$—S— | (a-6), |
| —CH$_2$—CH$_2$— | (a-2), | —CH$_2$—CH$_2$—S— | (a-7), |
| —CH$_2$—CH$_2$—CH$_2$— | (a-3), | —CH=N— | (a-8), |
| —CH$_2$—O— | (a-4), | —N=N— | (a-9), or |
| —CH$_2$—CH$_2$—O— | (a-5), | —CO—NH— | (a-10); | wherein optionally one hydrogen atom may be replaced by $C_{1-4}$alkyl or $Ar^1$;
$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy $C_{1-6}$alkyloxy, $C_{1-6}$alkyloxy$C_{1-6}$alkyloxy, $C_{1-6}$alkyloxycarbonyl, amino$C_{1-6}$alkyloxy, mono- or di($C_{1-6}$alkyl)amino $C_{1-6}$alkyloxy, $Ar^2$, $Ar^2$—$C_{1-6}$alkyl, $Ar^2$-oxy, $Ar^2$—$C_{1-6}$alkyloxy; or
when on adjacent positions $R^1$ and $R^2$ taken together may form a bivalent radical of formula

| —O—CH$_2$—O— | (b-1), |
| —O—CH$_2$—CH$_2$—O— | (b-2), |
| —O—CH=CH— | (b-3), |
| —O—CH$_2$—CH$_2$— | (b-4), |
| —O—CH$_2$—CH$_2$—CH$_2$— | (b-5), or |
| —CH=CH—CH=CH— | (b-6); |

$R^3$ and $R^4$ each independently are hydrogen, halo, cyano, $C_{1-6}$alkyl, $C_{1-6}$alkyloxy, $Ar^3$-oxy, $C_{1-6}$alkylthio, di($C_{1-6}$alkyl)amino, trihalomethyl, trihalomethoxy, or when on adjacent positions $R^3$ and $R^4$ taken together may form a bivalent radical of formula

| —O—CH$_2$—O— | (c-1), |
| —O—CH$_2$—CH$_2$—O— | (c-2), or |
| —CH=CH—CH=CH— | (c-3); |

$R^5$ is a radical of formula

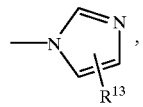  (d-1)

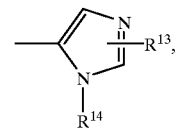  (d-2)

wherein $R^{13}$ is hydrogen, halo, $Ar^4$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, $C_{1-6}$alkyloxycarbonyl, $C_{1-6}$alkylS(O)$C_{1-6}$alkyl or $C_{1-6}$alkylS(O)$_2C_{1-6}$alkyl; $R^{14}$ is hydrogen, $C_{1-6}$alkyl or di($C_{1-4}$alkyl)aminosulfonyl;
$R^6$ is hydrogen, hydroxy, halo, $C_{1-6}$alkyl, cyano, halo$C_{1-6}$alkyl, hydroxy$C_{1-6}$alkyl, cyano$C_{1-6}$alkyl, amino$C_{1-6}$alkyl, $C_{1-6}$alkyloxy$C_{1-6}$alkyl, $C_{1-6}$alkylthio$C_{1-6}$alkyl, aminocarbonyl-$C_{1-6}$alkyl, $C_{1-6}$alkyloxycarbonyl $C_{1-6}$alkyl, $C_{1-6}$alkylcarbonyl$C_{1-6}$alkyl, $C_{1-6}$alkyloxycarbonyl, mono- or di($C_{1-6}$alkyl)amino $C_{1-6}$alkyl, $Ar^5$, $Ar^5$—$C_{1-6}$alkyloxy$C_{1-6}$alkyl; or a radical of formula

| —O—$R^7$ | (e-1), |
| —S—$R^7$ | (e-2), or |
| —N—$R^8R^9$ | (e-3); | wherein
$R^7$ is hydrogen, $C_{1-6}$alkyl, $C_{1-6}$alkylcarbonyl, $Ar^6$, $Ar^6$—$C_{1-6}$alkyl, $C_{1-6}$alkyloxycarbonyl$C_{1-6}$alkyl, or a radical of formula —Alk—$OR^{10}$ or —Alk—$NR^{11}R^{12}$;
$R^8$ is hydrogen, $C_{1-6}$alkyl, $Ar^7$ or $Ar^7$—$C_{1-6}$alkyl;
$R^9$ is hydrogen, $C_{1-6}$alkyl, $C_{1-6}$alkylcarbonyl, $C_{1-6}$alkyloxycarbonyl, $C_{1-6}$alkylaminocarbonyl, $Ar^8$, $Ar^8$-$C_{1-6}$alkyl, $C_{1-6}$alkylcarbonyl-$C_{1-6}$alkyl, $Ar^8$-carbonyl, $Ar^8$—$C_{1-6}$alkylcarbonyl, aminocarbonylcarbonyl, $C_{1-6}$alkyloxy $C_{1-6}$alkylcarbonyl, hydroxy, $C_{1-6}$alkyloxy, aminocarbonyl, di($C_{1-6}$alkyl)amino$C_{1-6}$alkylcarbonyl, amino, $C_{1-6}$alkylamino, $C_{1-6}$alkylcarbonylamino, or a radical or formula —Alk—$OR^{10}$ or —Alk—$NR^{11}R^{12}$;
wherein Alk is $C_{1-6}$alkanediyl;

$R^{10}$ is hydrogen, $C_{1-6}$alkyl, $C_{1-6}$alkylcarbonyl, hydroxy$C_{1-6}$alkyl, $Ar^9$ or $Ar^9$—$C_{1-6}$alkyl;

$R^{11}$ is hydrogen, $C_{1-6}$alkyl, $C_{1-6}$alkylcarbonyl, $Ar^{10}$ or $Ar^{10}$—$C_{1-6}$alkyl;

$R^{12}$ is hydrogen, $C_{1-6}$alkyl, $Ar^{11}$ or $Ar^{11}$-$C_{1-6}$alkyl; and $Ar^1$ to $Ar^{11}$ are each independently selected from phenyl; or phenyl substituted with halo, $C_{1-6}$alkyl, $C_{1-6}$alkyloxy or trifluoromethyl.

2. A compound according to claim 1 wherein the dotted line represents an optional bond; X is O or S; $R^1$ and $R^2$ are each independently selected from hydrogen, halo, $C_{1-6}$alkyl, $C_{1-6}$alkyloxy, trihalomethyl or trihalomethoxy; $R^3$ and $R^4$ are each independently selected from hydrogen, halo, $C_{1-6}$alkyl, $C^{1-6}$alkyloxy, trihalomethyl or trihalomethoxy; $R^5$ a radical of formula (d-1) wherein $R^{13}$ is hydrogen or $R^5$ is a radical of formula (d-2) wherein $R^{13}$ is hydrogen or $C_{1-6}$alkyl and $R^{14}$ is hydrogen or $C_{1-6}$alkyl; $R^6$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, or a radical of formula —$NR^8R^9$ wherein $R^8$ is hydrogen or $C_{1-6}$alkyl and $R^9$ is hydrogen, $C_{1-6}$alkyl, $C_{1-6}$alkyloxy or $C_{1-6}$alkyloxy $C_{1-6}$alkylcarbonyl.

3. A compound according to any of claim 1 wherein X is oxygen; the dotted line represents a bond; $R^1$ is 3-halo; $R^2$ is hydrogen; $R^3$ is 4-halo; $R^4$ is hydrogen; $R^5$ a radical of formula (d-1) wherein $R^{13}$ is hydrogen or $R^5$ is a radical of formula (d-2) wherein $R^{13}$ is hydrogen and $R^{14}$ is $C_{1-4}$alkyl; $R^6$ is hydrogen, halo, hydroxy or amino; and —A— is (a-1), (a-2) or (a-3).

4. A compound according to claim 1 wherein the compound is 7-(3-chlorophenyl)-9-[(4-chlorophenyl)-1H-imidazol-1-ylmethyl]-2,3-dihydro-1H,5H-benzo[ij]quinolizin-5-one;

7-(3-chlorophenyl)-9-[(4-chlorophenyl)-1H-imidazol-1-ylmethyl]-1,2-dihydro-4H-pyrrolo[3,2,-ij]quinoline-4-one;

8-[amino(4-chlorophenyl)(1-methyl-1H-imidazol-5-yl) methyl]-6-(3-chlorophenyl)-1,2-dihydro-4H-pyrrolo[3,2, 1-ij]quinolin-4-one; or 8-[amino(4-chlorophenyl)(1-methyl-1H-imidazol-5-yl) methyl]-6-(3-chlorophenyl)-2,3-dihydro-1H,5H-benzo [ij]quinolizin-5-one; a stereoisomeric form or a pharmaceutically acceptable acid addition salt thereof.

5. A pharmaceutical composition comprising a pharmaceutically acceptable carrier, and as active ingredient a therapeutically effective amount of a compound as described in claim 1.

6. A compound of formula (II)

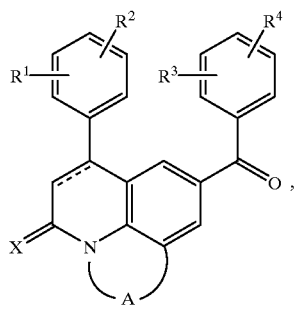

(II)

an acid addition salt or a stereochemically isomeric form thereof, wherein the dotted line represents an optional bond;

X is oxygen or sulfur;

—A— is bivalent radical of formula

| —CH=CH— | (a-1), | —CH$_2$—S— | (a-6), |
|---|---|---|---|
| —CH$_2$—CH$_2$— | (a-2), | —CH$_2$—CH$_2$—S— | (a-7), |
| —CH$_2$—CH$_2$—CH$_2$— | (a-3), | —CH=N— | (a-8), |
| —CH$_2$—O— | (a-4), | —N=N— | (a-9), or |
| —CH$_2$—CH$_2$—O— | (a-5), | —CO—NH— | (a-10); | wherein optionally one hydrogen atom may be replaced by $C_{1-4}$alkyl or $Ar^1$;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyl-oxy, $C_{1-6}$alkyloxy$C_{1-6}$alkyloxy, $C_{1-6}$alkyloxycarbonyl, amino$C_{1-6}$alkyloxy, mono-or di($C_{1-6}$alkyl)amino $C_{1-6}$alkyloxy, $Ar^2$, $Ar^2$—$C_{1-6}$alkyl, $Ar^2$-oxy, $Ar^2$-$C_{1-6}$alkyloxy; or when on adjacent positions $R^1$ and $R^2$ taken together may form a bivalent radical of formula

| —O—CH$_2$—O— | (b-1), |
|---|---|
| —O—CH$_2$—CH$_2$—O— | (b-2), |
| —O—CH=CH— | (b-3), |
| —O—CH$_2$—CH$_2$— | (b-4), |
| —O—CH$_2$—CH$_2$—CH$_2$— | (b-5), or |
| —CH=CH—CH=CH— | (b-6); and |

$R^3$ and $R^4$ each independently are hydrogen, halo, cyano, $C_{1-6}$alkyl, $C_{1-6}$alkyloxy, $Ar^3$-oxy, $C_{1-6}$alkylthio, di($C_{1-6}$alkyl)amino, trihalomethyl, trihalomethoxy, or when on adjacent positions $R^3$ and $R^4$ taken together may form a bivalent radical of formula

| —O—CH$_2$—O— | (c-1), |
|---|---|
| —O—CH$_2$—CH$_2$—O— | (c-2), or |
| —CH=CH—CH=CH— | (c-3). |

7. A process for preparing a compound formula (I) as claimed in claim 1, wherein the process comprises at least one of the following steps:

a) an intermediate ketone of formula (II) is reacted with an intermediate of formula (III-1) or (III-2) in the presence of a strong base and in the presence an silanederivative, optionally followed by removal of a protective group PG;

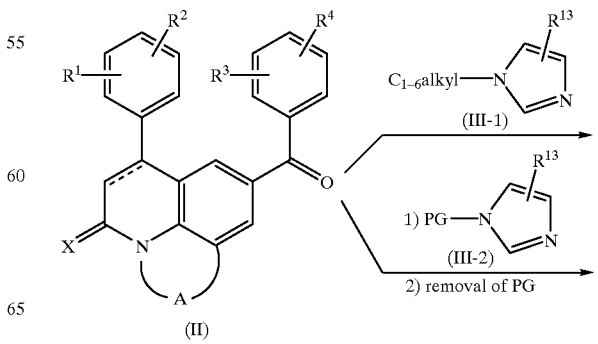

(II)

-continued

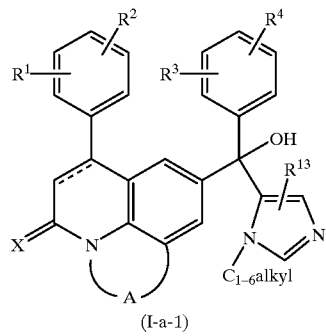

(I-a-1)

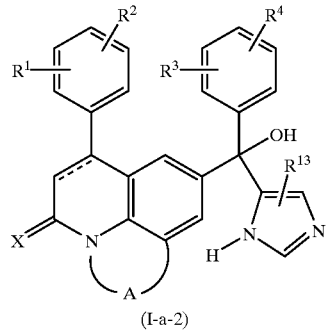

(I-a-2)

b) compounds of formula (I-a), defined as compounds of formula (I) wherein $R^6$ is hydroxy, are converted to compounds of formula (I-c) wherein $R^6$ is halo, optionally followed by treatment with an intermediate of formula H—$NR^8R^9$ yielding compounds of formula (I-d);

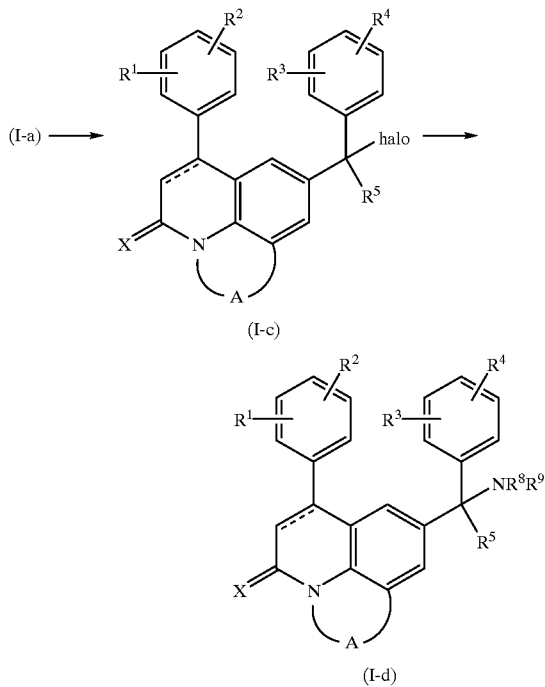

c) an intermediate of formula (XVM) is N-alkylated with an intermediate of formula (XVII) in a reaction-inert solvent and, optionally in the presence of a base;

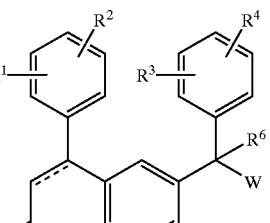

(XVII)

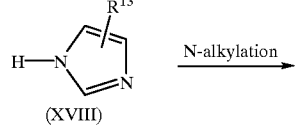

(XVIII)

N-alkylation →

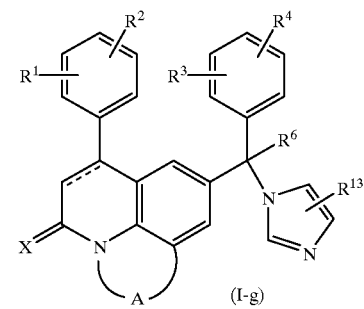

(I-g)

d) an intermediate of formula (XIX) is N-alkylated with a compound of formula (XVI);

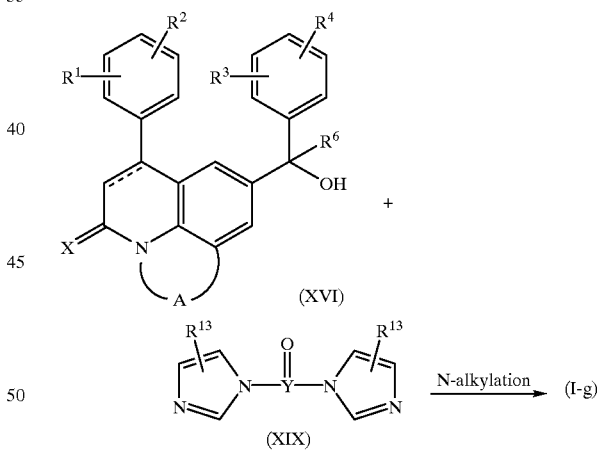

wherein in the above reaction schemes the dotted line and the radicals X, $R^1$, $R^2$, $R^3$, $R^4$, $R^5$, $R^6$, $R^8$, $R^9$ and $R^3$ and —A— are as defined in claim 1, W is an leaving group and Y is carbon or sulfur;

e) or; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

8. A process for preparing an intermediate compound of formula (II) as claimed in claim 6 wherein a) an intermediate of formula (VI) is treated with an intermediate of formula (V) in the presence of polyphosphoric acid (PPA);

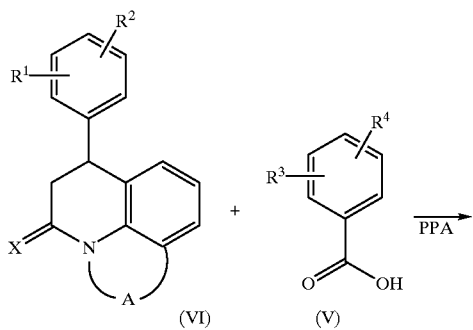

b) or, an intermediate of formula (IV) is treated with an intermediate of formula (V) in the presence of polyphosphoric acid (PPA);

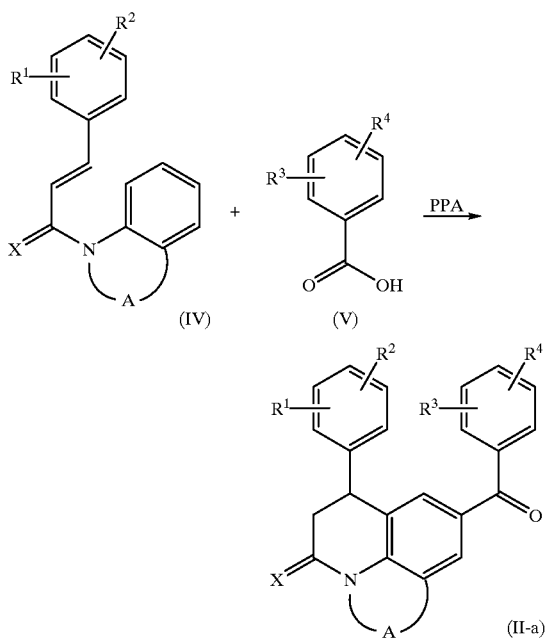

c) intermediates of formula (II-a), defined as intermediates of formula (II) wherein the dotted line does not represent a bond, is converted into intermediates of formula (II-b), defined as an intermediate of formula (II) wherein the dotted line represents a bond, by oxidation

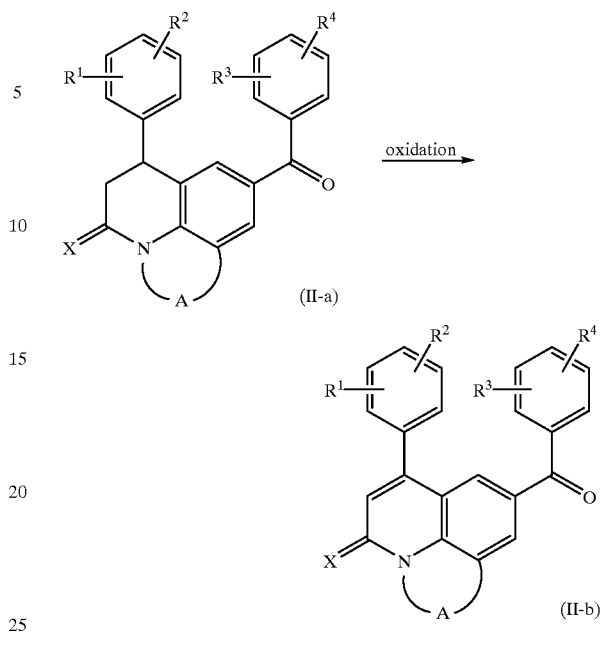

wherein in the above reaction schemes

X is oxygen or sulfur;

—A— is bivalent radical of formula

| | | | |
|---|---|---|---|
| —CH=CH— | (a-1), | —CH$_2$—S— | (a-6), |
| —CH$_2$—CH$_2$— | (a-2), | —CH$_2$—CH$_2$—S— | (a-7), |
| —CH$_2$—CH$_2$—CH$_2$— | (a-3), | —CH=N— | (a-8), |
| —CH$_2$—O— | (a-4), | —N=N— | (a-9), or |
| —CH$_2$—CH$_2$—O— | (a-5), | —CO—NH— | (a-10); | wherein optionally one hydrogen atom may be replaced by $C_{1-4}$alkyl or $Ar^1$;

$R^1$ and $R^2$ each independently are hydrogen, hydroxy, halo, cyano, $C_{1-6}$alkyl, trihalomethyl, trihalomethoxy, $C_{2-6}$alkenyl, $C_{1-6}$alkyloxy, hydroxy$C_{1-6}$alkyl-oxy, $C_{1-6}$alkyloxy$C_{1-6}$alkyloxy, $C_{1-6}$alkyloxycarbonyl, amino$C_{1-6}$alkyloxy, mono- or di ($C_{1-6}$alkyl)amino $C_{1-6}$alkyloxy, $Ar^2$, $Ar^2$—$C_{1-6}$alkyl, $Ar^2$-oxy, $Ar^2$—$C_{1-6}$alkyloxy; or when on adjacent positions $R^1$ and $R^2$ taken together may form a bivalent radical of formula

| | |
|---|---|
| —O—CH$_2$—O— | (b-1), |
| —O—CH$_2$—CH$_2$—O— | (b-2), |
| —O—CH=CH— | (b-3), |
| —O—CH$_2$—CH$_2$— | (b-4), |
| —O—CH$_2$—CH$_2$—CH$_2$— | (b-5), or |
| —CH=CH—CH=CH— | (b-6); and |

$R^3$ and $R^4$ each independently are hydrogen, halo, cyano, $C_{1-6}$alkyl, $C_{1-6}$alkyloxy, $Ar^3$-oxy, $C_{1-6}$alkylthio, di($C_{1-6}$alkyl)amino, trihalomethyl, trihalomethoxy, or when on adjacent positions $R^3$ and $R^4$ taken together may form a bivalent radical of formula

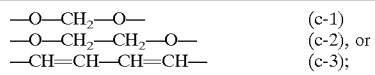

d) or; a compound of formula (II-a) is converted into a pharmaceutically acceptable acid addition salt, or conversely, an acid addition salt of a compound of formula (II-a) is converted into a free base form with alkali; and, optionally, preparing stereochemically isomeric forms thereof.

9. A method for inhibiting the abnormal growth of cells by inhibition of farnesyl transferase in a mammal in need thereof comprising administering to said mammal an effective amount of a compound as claimed in claim 1.

10. A method for inhibiting tumor growth by inhibition of farnesyl transferase in a mammal in need thereof comprising administering to said mammal an effective amount of a compound as claimed in claim 1.

11. A method for inhibiting the growth of tumors expressing an activated ras oncogene by inhibition of farnesyl transferase in a mammal in need thereof comprising administering to said mammal a compound as claimed in claim 1.

* * * * *